US011937653B2

(12) United States Patent
Kaiserman et al.

(10) Patent No.: US 11,937,653 B2
(45) Date of Patent: Mar. 26, 2024

(54) SMART MASK

(71) Applicant: Vitiprints, LLC, New York, NY (US)

(72) Inventors: Terrance Kaiserman, Loxahatchee, FL (US); John Gentile, Montclair, NJ (US); Andrew Ferber, New York, NY (US); Anthony Gentile, New York, NY (US); Mitchell Modell, Bridgehampton, NY (US)

(73) Assignee: Vitiprints, LLC, New York, NY (US)

( * ) Notice: Subject to any disclaimer, the term of this patent is extended or adjusted under 35 U.S.C. 154(b) by 0 days.

(21) Appl. No.: 17/332,367

(22) Filed: May 27, 2021

(65) Prior Publication Data

US 2022/0007754 A1 Jan. 13, 2022

Related U.S. Application Data

(60) Provisional application No. 63/049,820, filed on Jul. 9, 2020.

(51) Int. Cl.
*A41D 13/11* (2006.01)
*A41D 31/14* (2019.01)
(Continued)

(52) U.S. Cl.
CPC ............ *A41D 13/11* (2013.01); *A41D 31/145* (2019.02); *A41D 31/305* (2019.02); *A61B 5/01* (2013.01); *D06N 3/0002* (2013.01); *D06N 3/0059* (2013.01); *D06N 3/0063* (2013.01); *D06N 3/0068* (2013.01); *D06N 3/042* (2013.01);
(Continued)

(58) Field of Classification Search
CPC .. D06N 3/0059; D06N 3/0063; D06N 3/0002; D06N 3/0068; D06N 3/042; D10B 2401/13; A41D 13/11; A41D 13/145; A41D 31/305; A41D 31/145; A62B 23/02; A62B 23/025; A62B 18/02; Y10T 442/109; Y10T 442/174; Y10T 442/2525; B32B 5/26; B32B 5/265; B32B 5/266–271; B32B 7/12
See application file for complete search history.

(56) References Cited

U.S. PATENT DOCUMENTS 1,925,914 A 9/1933 Waldemar
3,532,534 A * 10/1970 Wolff ..................... D21H 19/60
427/364
(Continued)

FOREIGN PATENT DOCUMENTS

CN 102061625 B 11/2012
CN 103637431 A * 3/2014
(Continued)

OTHER PUBLICATIONS

"CN103637431_Machine Translation" is a machine translation of CN-103637431-A. (Year: 2014).*
(Continued)

*Primary Examiner* — Larissa Rowe Emrich
(74) *Attorney, Agent, or Firm* — Lerner David LLP

(57) ABSTRACT

A face mask includes a non-woven fabric filter configured to be worn on a user's face. A composition with anti-viral properties is arranged on the fabric. The composition preferably includes anti-viral oils and an anti-viral metal such as copper or copper oxide.

19 Claims, 13 Drawing Sheets

(51) Int. Cl.
  *A41D 31/30* (2019.01)
  *A61B 5/01* (2006.01)
  *D06N 3/00* (2006.01)
  *D06N 3/04* (2006.01)
  *A62B 23/02* (2006.01)

(52) U.S. Cl.
  CPC ........ *A62B 23/025* (2013.01); *D10B 2101/20* (2013.01); *D10B 2401/12* (2013.01); *D10B 2501/04* (2013.01); *D10B 2509/00* (2013.01); *Y10T 442/109* (2015.04); *Y10T 442/174* (2015.04); *Y10T 442/2525* (2015.04)

(56) References Cited

U.S. PATENT DOCUMENTS

| | | | | |
|---|---|---|---|---|
| 3,828,366 | A * | 8/1974 | Conrad | A45D 44/12 2/174 |
| 5,162,410 | A * | 11/1992 | Sweet | A61K 9/7069 524/266 |
| 5,306,435 | A | 4/1994 | Ishikawa et al. | |
| 5,478,387 | A | 12/1995 | Dragner et al. | |
| 5,605,651 | A * | 2/1997 | Balzer | A61K 8/068 424/401 |
| 5,636,628 | A * | 6/1997 | Barnum | A41D 13/1115 128/206.12 |
| 5,853,879 | A | 12/1998 | Takamiya et al. | |
| 6,046,260 | A | 4/2000 | Hoover | |
| 6,596,034 | B1 | 7/2003 | Crawford et al. | |
| 6,638,319 | B2 | 10/2003 | Sanduja et al. | |
| 6,645,256 | B2 | 11/2003 | Sanduja et al. | |
| 6,660,044 | B2 | 12/2003 | Igarashi et al. | |
| 6,673,118 | B2 | 1/2004 | DuVal et al. | |
| 6,676,710 | B2 | 1/2004 | Smith et al. | |
| 6,719,809 | B2 | 4/2004 | Payet | |
| 7,078,075 | B1 * | 7/2006 | Werenicz | B32B 7/12 156/244.11 |
| 7,226,607 | B2 | 6/2007 | Uchiyama et al. | |
| 7,335,613 | B2 | 2/2008 | Cottrell et al. | |
| 7,390,774 | B2 | 6/2008 | Ghosh et al. | |
| 7,648,534 | B2 | 1/2010 | Li et al. | |
| 7,678,155 | B2 | 3/2010 | Yamamoto et al. | |
| 7,717,963 | B2 | 5/2010 | Yamaguchi et al. | |
| 7,758,656 | B2 | 7/2010 | Enomoto et al. | |
| 7,846,856 | B2 | 12/2010 | Ghosh et al. | |
| 7,956,025 | B2 | 6/2011 | Copete Vidal et al. | |
| 7,968,619 | B2 | 6/2011 | Cottrell et al. | |
| 8,007,834 | B2 | 8/2011 | Collin et al. | |
| 8,147,707 | B2 | 4/2012 | Payne et al. | |
| 8,349,748 | B2 | 1/2013 | Chen et al. | |
| 8,579,829 | B2 * | 11/2013 | Feldman | A61B 5/0803 600/537 |
| 8,685,304 | B2 | 4/2014 | Arora et al. | |
| 8,690,964 | B2 | 4/2014 | Kramer et al. | |
| 8,833,366 | B2 | 9/2014 | Colombo et al. | |
| 8,968,793 | B2 | 3/2015 | Hadar et al. | |
| 10,821,680 | B2 | 11/2020 | Roman et al. | |
| 2002/0142027 | A1 * | 10/2002 | Gueret | A61M 35/10 424/443 |
| 2004/0026318 | A1 * | 2/2004 | Lemaire | C11B 9/025 210/634 |
| 2004/0071757 | A1 * | 4/2004 | Rolf | A61K 9/7061 424/443 |
| 2004/0072948 | A1 | 4/2004 | Sanduja et al. | |
| 2008/0193496 | A1 * | 8/2008 | Gabbay | C08J 3/22 424/404 |
| 2009/0145434 | A1 * | 6/2009 | Herrmann | A61M 15/085 128/203.29 |
| 2012/0060258 | A1 * | 3/2012 | Stewart | A41D 13/1107 2/206 |
| 2012/0076942 | A1 * | 3/2012 | Liang | A01N 59/16 427/383.1 |
| 2012/0111330 | A1 | 5/2012 | Gartner | |
| 2012/0199142 | A1 * | 8/2012 | Nagao | A41D 13/1115 128/863 |
| 2014/0030203 | A1 * | 1/2014 | Dombeck | A61K 8/922 424/65 |
| 2014/0308867 | A1 | 10/2014 | Van Emmerick et al. | |
| 2015/0225525 | A1 | 8/2015 | Samuels | |
| 2015/0335012 | A1 | 11/2015 | Chen et al. | |
| 2016/0030579 | A1 * | 2/2016 | Carty | A61K 45/06 424/443 |
| 2016/0130747 | A1 * | 5/2016 | Hanison | D06N 3/0063 442/76 |
| 2018/0208778 | A1 | 7/2018 | Liu et al. | |

FOREIGN PATENT DOCUMENTS

| | | | |
|---|---|---|---|
| CN | 102418271 B | 8/2015 | |
| CN | 104928826 B | 5/2016 | |
| CN | 103509364 B | 8/2016 | |
| CN | 106436328 A | 2/2017 | |
| CN | 107988692 A | 5/2018 | |
| CN | 109235041 A | 1/2019 | |
| CN | 112021340 A | 12/2020 | |
| EP | 3061865 A1 | 8/2016 | |
| ES | 2765374 A1 | 6/2020 | |
| JP | 2019119945 A | 7/2019 | |
| KR | 101598969 B1 | 3/2016 | |
| KR | 101858348 B1 | 5/2018 | |
| KR | 101910772 B1 | 10/2018 | |
| WO | 200143804 A1 | 6/2001 | |
| WO | 2007120509 A2 | 10/2007 | |
| WO | 2010138426 A1 | 12/2010 | |
| WO | WO-2017180620 A1 * | 10/2017 | ............ A41D 31/04 |

OTHER PUBLICATIONS

"Difference between Surfactant and Emulsifier." Nanjing Chemical Material Corp., 2019, https://www.njchm.com/service/difference-between-surfactant-and-emulsifier.html. (Year: 2017).*

International Search Report for Appln. No. PCT/US2021/040837 dated Oct. 22, 2021 (3 pages).

* cited by examiner

SMART MASK

CROSS REFERENCE TO RELATED APPLICATION

The present application claims the benefit of the filing date of U.S. Provisional Patent Application No. 63/049,820 filed Jul. 9, 2020, the disclosure of which is hereby incorporated herein by reference.

BACKGROUND OF THE INVENTION

Face masks are commonly used to prevent the inhalation of debris and transmission of respiratory infections. Known masks typically consist of a fabric or other relatively porous material, including various polymers, for covering the wearer's nose and mouth along with features to secure the mask to the wearer's head. Such masks provide a simple filter between ambient air and the wearer's airways, but little else.

BRIEF SUMMARY OF THE INVENTION

According to an aspect of the invention, a mask may include an antiviral layer and/or a visual indicator of a wearer's temperature. The visual indicator preferably presents temperature as measured by a thermistor integrated with the mask. The visual indicator may also include thermochromic ink arranged to change color at a particular temperature.

The thermochromic ink or other visual indicator may be arranged to form one or more patches, each patch configured to visibly activate at a different temperature of the wearer. Visible activation may include, for example, color change of thermochromic ink or illumination of a lighting element. The patches may be accompanied by corresponding markers, such as numbers to indicate specific temperatures, informing an observer of the meaning of the patches. An interval indicator may include a lighting element that may blink or flash according to a rhythm that varies according to the temperature of the wearer.

Temperature responsive illumination may be provided by a circuit including one or more thermistors connected to the lighting element, such as an LED. The thermistor may be coupled with a capacitor such that power is supplied to the lighting element on an interval that varies as an analog function of the temperature of the thermistor. The circuit may further include a printed circuit board (PCB) with a microprocessor configured with control logic for accepting the temperature of the thermistor as an input and for outputting a flashing or blinking rhythm for the lighting element.

The antiviral layer may be constructed of a material having antiviral properties, such as a fabric or fiber mesh dip-coated in copper or another antiviral composition. The mask may include inert layers on either side of the antiviral layer to facilitate additional filtering or comfort for the user, or for aesthetic purposes.

According to another aspect, a face mask may comprise a filter configured to stand between ambient air and a wearer's airways and including a semipermeable antiviral layer, and a visual temperature indicator.

In another arrangement according to any of the foregoing, the indicator may include a patch of thermochromic ink.

In another arrangement according to any of the foregoing, the indicator may include multiple patches, each configured to visibly activate at a different temperature.

In another arrangement according to any of the foregoing, each of the patches may include thermochromic ink.

In another arrangement according to any of the foregoing, the indicator may include at least two visible markers, each of the markers being adjacent to a different one of the patches.

In another arrangement according to any of the foregoing, each of the markers may be configured to indicate a temperature of a wearer's body at which the corresponding patch is configured to visibly activate.

In another arrangement according to any of the foregoing, the indicator may include an electronic lighting element.

In another arrangement according to any of the foregoing, the lighting element may be electronically configured to light according to a rhythm that varies as a function of a measured temperature.

In another arrangement according to any of the foregoing, the measured temperature may be acquired by a thermistor integrated in the circuit.

In another arrangement according to any of the foregoing, the rhythm may vary according to a first function of temperature when the measured temperature is within a first range, and the rhythm varies according to a second function of temperature when the measured temperature is within a second range.

In another arrangement according to any of the foregoing, the circuit may be configured to control the lighting element to switch between lit and unlit on an interval that decreases as the measured temperature increases.

In another arrangement according to any of the foregoing, the antiviral layer may be a porous material dip-coated with copper.

In another arrangement according to any of the foregoing, the filter may include an outer layer, and the mask may include a lighting element disposed between the antiviral layer and the outer layer.

According to another aspect, coated fabric article may comprise a coating provided by curing a mixture applied to the article. The mixture may comprise a resin binder, oils having antiviral properties, and emulsifiers providing no more than 2% of the mixture by weight acting to create an emulsion within the mixture, the emulsion including the binder and the oils.

In another arrangement according to any of the foregoing, the oils may be any one or any combination of cinnamon oil, tea tree oil, eucalyptus oil, thyme oil, and clove oil.

In another arrangement according to any of the foregoing, the mixture may further comprise antiviral metal.

In another arrangement according to any of the foregoing, the mixture may include more oil than metal by weight.

In another arrangement according to any of the foregoing, the curing may have been ceased before the binder was cross-linked.

In another arrangement according to any of the foregoing, an item of personal protective equipment may comprise the coated fabric article.

In another arrangement according to any of the foregoing, the item may be a breathing mask and the article may be a breathable filter portion of the mask.

In another aspect, a method of manufacturing a coated fabric article may comprise applying a mixture to an article. The mixture may comprise a resin binder, oil having antiviral properties, water providing no more than two thirds of the mixture by weight, emulsifiers providing from 0.5% to 2% of the mixture by weight, and an emulsion within the mixture, the emulsion including the binder and the oil. The method may further comprise curing the mixture after the mixture has been applied to the article.

In another arrangement according to any of the foregoing, the oil may be any one or any combination of cinnamon oil, tea tree oil, eucalyptus oil, thyme oil, and clove oil.

In another arrangement according to any of the foregoing, the mixture may further comprise antiviral metal or antiviral metal oxide.

In another arrangement according to any of the foregoing, the antiviral metal or antiviral metal oxide may be copper.

In another arrangement according to any of the foregoing, the mixture may include more oil than metal by weight.

In another arrangement according to any of the foregoing, the curing step may include heating the mixture until the mixture is at least partially dehydrated and ceases before any cross-linking occurs within the binder.

In another arrangement according to any of the foregoing, the oil may include an undesired compound and a desired compound, the undesired compound being an aromatic compound having a first flashpoint and the desired compound being either or both of an aromatic compound and an antiviral compound and having a second flashpoint greater than the first flashpoint. A maximum temperature reached by the mixture during the curing step is between the first flashpoint and the second flashpoint.

In another arrangement according to any of the foregoing, the oil may be from 6% to 12% of the mixture by weight before the mixture is cured, or from 12% to 24% by weight of a coating on the article created by curing the mixture upon the article.

In another arrangement according to any of the foregoing, the article may be a breathable filter portion of a breathing mask.

In another aspect, a face mask may comprise a filter configured to stand between ambient air and a wearer's airways and including a semipermeable antiviral layer, the antiviral layer including a fabric treated with an active coating. The active coating may comprise a solidified resin, particles of a metal having antiviral properties dispersed within the resin, and oil dispersed within the resin in an unstable homogeneous mixture permitting the oil to gradually collect in a film on a surface of the coating.

In another arrangement according to any of the foregoing, the metal may be copper.

In another arrangement according to any of the foregoing, the mask may comprise a visual temperature indicator.

In another arrangement according to any of the foregoing, the indicator may include a patch of thermochromic ink.

In another arrangement according to any of the foregoing, the indicator may include an electronic lighting element.

In another arrangement according to any of the foregoing, the mask may include a thermistor, and the indicator may be configured to indicate a measured temperature acquired by the thermistor.

In another arrangement according to any of the foregoing, the oil may be an antiviral oil or antiviral oil blend.

In another arrangement according to any of the foregoing, the oil may be any one or any combination of cinnamon oil, tea tree oil, eucalyptus oil, thyme oil, and clove oil.

In another arrangement according to any of the foregoing, the unstable homogenous mixture may include propylene glycol.

In another arrangement according to any of the foregoing, the filter may further include an inert layer of fabric free of the active coating.

In another arrangement according to any of the foregoing, wherein the inert layer may be on a wearer-facing side of the filter.

In another aspect, an article may comprise a fabric coated with a composition. The composition may include a resin, oil having antiviral properties, an emulsifier, and metal particles having antiviral properties.

In another arrangement according to any of the foregoing, the oil may comprise cinnamon oil, tea tree oil, eucalyptus oil, thyme oil, and/or clove oil.

In another arrangement according to any of the foregoing, the resin may be an uncrosslinked polymer.

In another arrangement according to any of the foregoing, the antiviral metal particles may comprise copper or copper oxide.

In another arrangement according to any of the foregoing, the composition may include more oil than metal by weight.

In another arrangement according to any of the foregoing, the metal particles may be between 1 and 10 microns in diameter.

In another arrangement according to any of the foregoing, the oil may be 0.1% to 2% of the coating by weight.

In another arrangement according to any of the foregoing, the oil may comprise an essential oil from which at least one aromatic compound has been removed.

In another arrangement according to any of the foregoing, the oil may be present in an amount from 12% to 24% of the composition by weight.

In another arrangement according to any of the foregoing, the article may comprise a face mask and the fabric comprises an air-permeable filter of the face mask.

In another aspect, a face mask may comprise an air-permeable fabric configured to be placed on a user's face, a composition arranged on the fabric, the composition including a resin, metal particles having antiviral properties dispersed within the resin, an emulsifier dispersed within the resin, and oil having antiviral properties dispersed within the resin.

In another arrangement according to any of the foregoing, the metal may comprise copper.

In another arrangement according to any of the foregoing, the metal may comprise copper oxide.

In another arrangement according to any of the foregoing, the mask may comprise a temperature indicator.

In another arrangement according to any of the foregoing, the temperature indicator may comprise thermochromic ink or an electronic lighting element.

In another arrangement according to any of the foregoing, the temperature indicator may comprise a thermistor.

In another arrangement according to any of the foregoing, the composition may have a surface and the oil is unstable within the composition such that the oil gradually migrates to the surface.

In another arrangement according to any of the foregoing, the resin may further comprise a hot melt adhesive.

In another arrangement according to any of the foregoing, the fabric may be folded and adhered to itself by the hot melt adhesive.

In another arrangement according to any of the foregoing, the fabric may have an inner side configured to be placed adjacent a user's face and an outer side, the composition being arranged on the outer side of the fabric.

In another arrangement according to any of the foregoing, the fabric may have upper and lower edges and includes coating-free regions at the upper and lower edges

DETAILED DESCRIPTION

Figure 1:
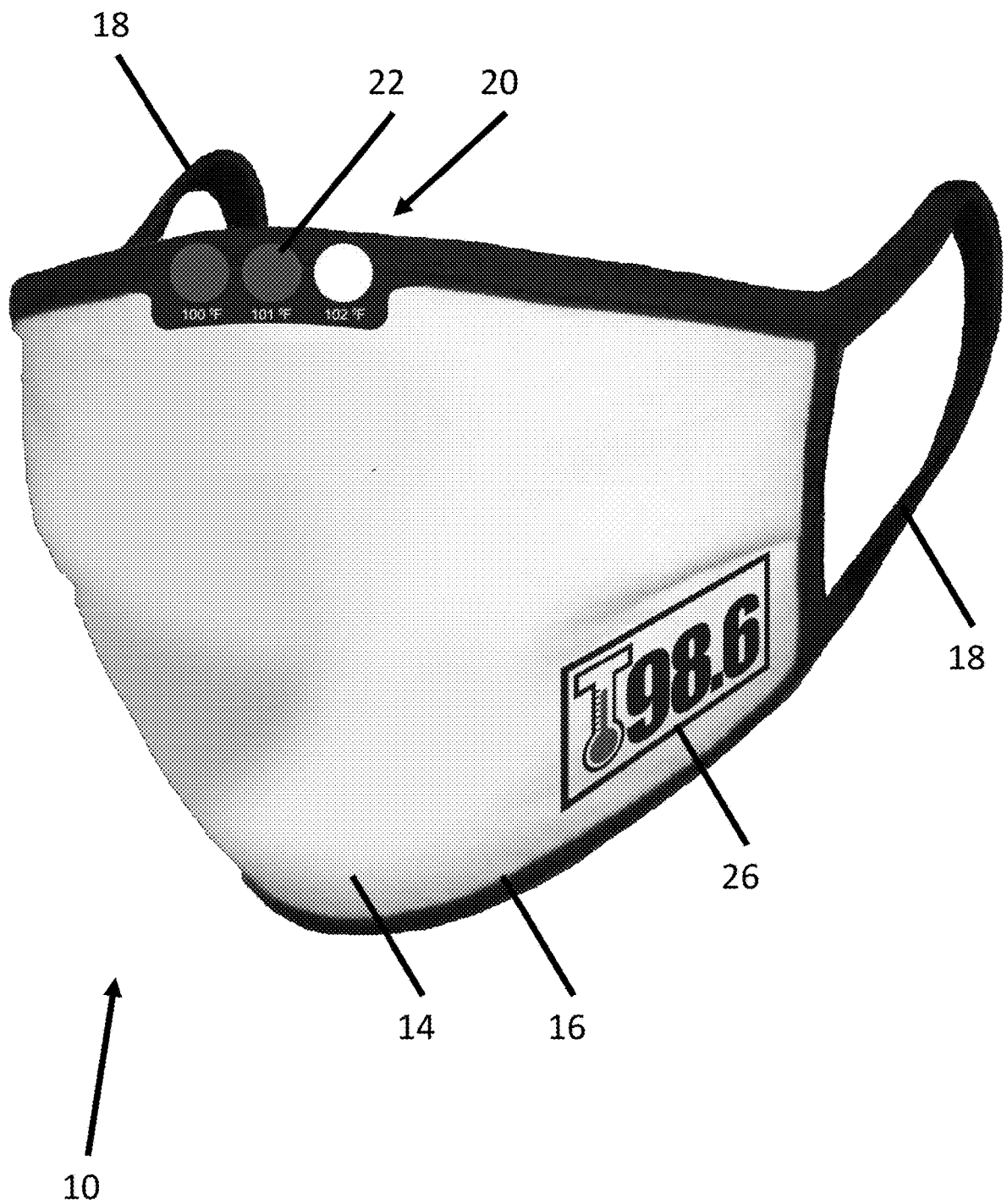
FIG. 1 is a perspective view of a breathing mask of FIG. 1.

An exemplary face mask 10 shown in FIG. 1 includes a permeable filter 14, a trim 16 around the filter 14, a pair of loops 18 connected to the trim 16 on opposite sides of the filter 14. The filter 14 is sized and shaped to cover the nose and mouth of a wearer. Though not visible in FIG. 1, the filter 14 includes an antiviral layer. The mask 10 further includes a cumulative indicator 22 and an interval indicator 26 both configured to visibly indicate the wearer's body temperature. The mask 10 of the illustrated example therefore includes both an antiviral layer and features for visibly indicating the body temperature of the wearer.

The cumulative indicator 22 and the interval indicator 26 therefore change appearance as a function of temperature. The cumulative indicator 22 has a plurality of predefined visible states each corresponding to one of a plurality of predefined temperature ranges, and can therefore indicate which one of the plurality of temperature ranges the wearer's body temperature falls within. The interval indicator 26 flashes in a pattern or rhythm that varies as a function of the wearer's body temperature, and may therefore represent the wearer's body temperature with more or less granularity than the cumulative indicator 22 depending on how the interval indicator 26 is configured.

The trim 16 extends around the edges of the filter 14 to prevent the filter 14 from fraying at its edges and to hold the multiple layers together. The loops 18 extend away from the filter 14 so they may be secured behind the wearer's head, such as by looping over the wearer's ears. The illustrated example further includes a bridge portion 20 in a portion of the trim 16 equidistant between the loops 18 for conforming the mask 10 to a bridge of the wearer's nose. The bridge portion 20 may include a plastically deformable element such as, for example, a metal wire.

Figure 2A:
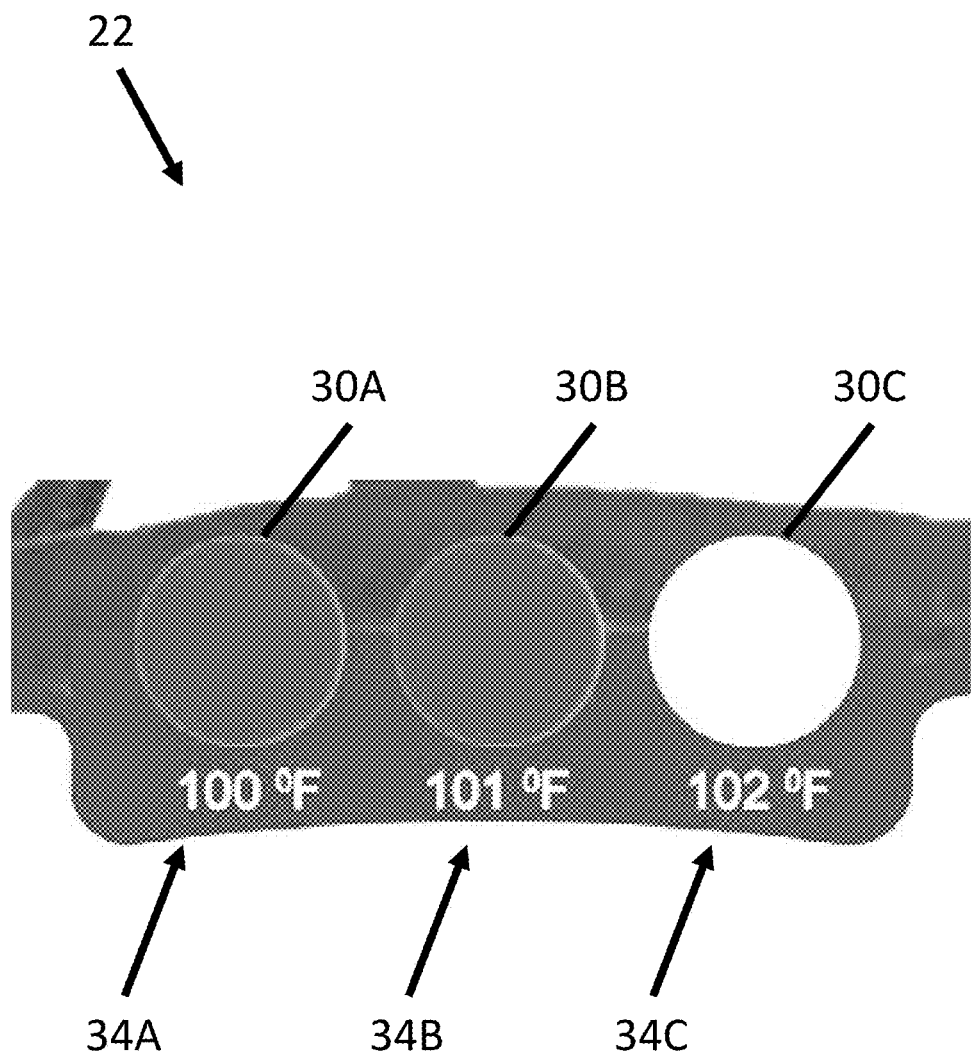
FIGS. 2A-2D illustrate cumulative temperature indicators for the mask of FIG. 1 according to be various arrangements.

The cumulative indicator 22 is shown in greater detail in FIG. 2A. The cumulative indicator 22 includes a first patch 30A, a second patch 30B, and a third patch 30C, arranged in a lateral row. The patches 30 are each configured to visibly activate at a different temperature. In various examples, visible activation is accomplished by a color change of thermochromic ink, illumination of a lighting element such as an LED, or any other feature or substance capable of producing a reversible visible change that can be tied to a specific temperature. Configuration of thermochromic ink patches to visibly activate at different temperatures includes formulating the ink of each patch to change color at a different temperature. Configuration of lighting elements to visibly activate at different temperatures may include connecting each element on a different circuit configured to power the element at a different temperature, or connecting all elements to a single circuit including a controller that selectively powers each element at a different temperature.

The patches 30 are each accompanied by a respective first marker 34A, second marker 34B, and third marker 34C. The markers 34 apprise an observer of the meaning of the corresponding patch 30. The markers 34 each display a temperature in degrees Fahrenheit equal, or approximately equal within a tolerance of ±0.5 degrees, to the body temperature of the wearer at which the corresponding patch 30 will visibly activate. Preparation of the patches 30 during construction of the mask 10 can include calibration of the feature that visibly activates, such as adjusting for the probable difference between the actual body temperature of the wearer and the temperature at the patch 30 itself such that the markers 34 will accurately represent the body temperature of the wearer.

Because the average temperature of a healthy human is commonly known to be about 98.6° Fahrenheit, the markers on the patches will indicate to an observer whether the wearer has an elevated body temperature. Elevated body temperatures frequently result from disease, so a visible indicator of the wearer's body temperature can enable the wearer and any observers to take appropriate precautions and slow the rate at which infections spread throughout a population. The markers 34 can also be used in extreme temperature conditions that the wearer is in danger of heat related illness, and should seek a cooler area. In further examples, at least one of the patches 30 can be set to activate at a body temperature of the wearer below 98.6° Fahrenheit, and an accompanying marker 34 can serve to notify observers that the wearer is experiencing hypothermia.

Figure 2B:
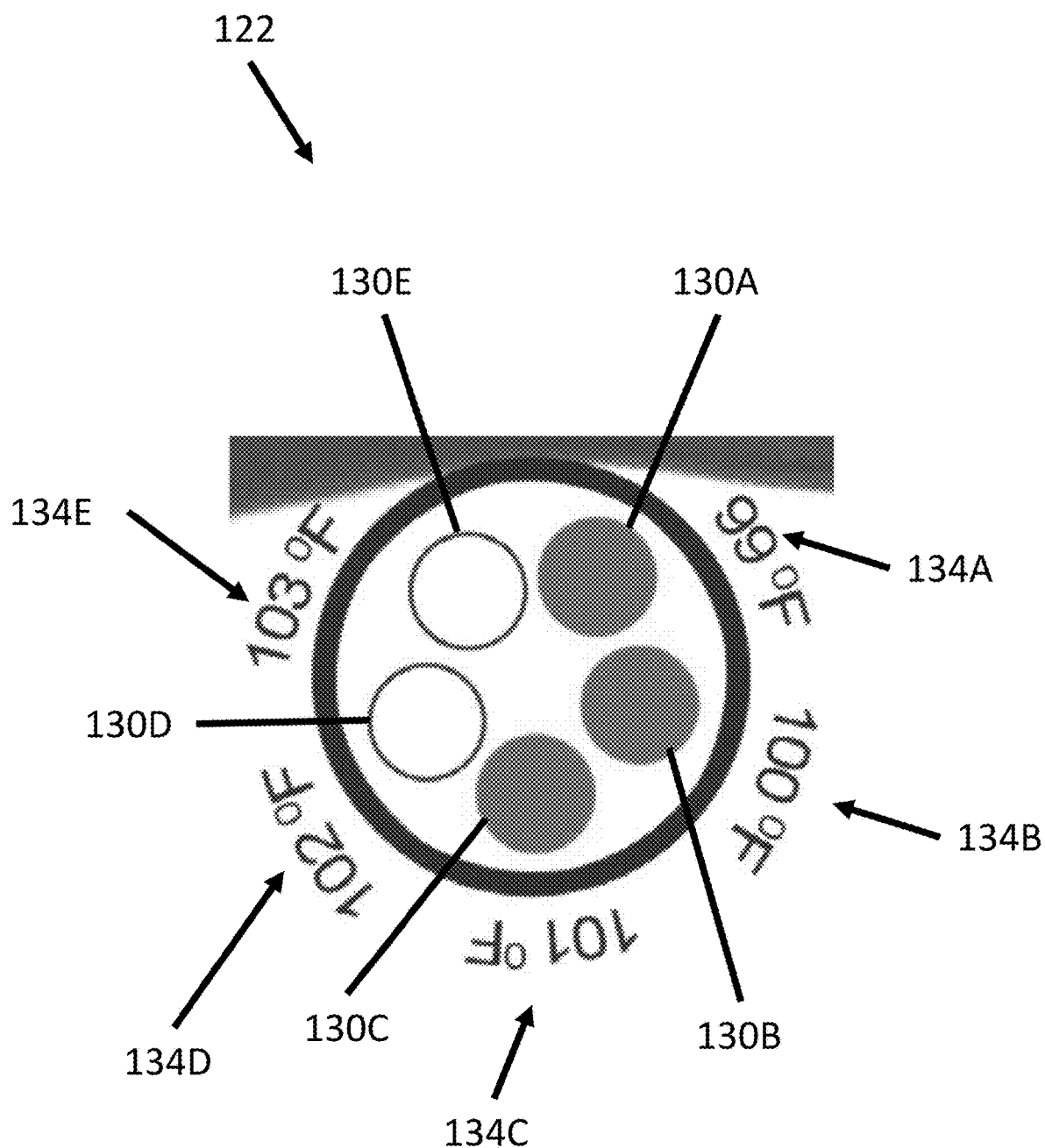

A cumulative indicator 122 according to a second arrangement is shown in FIG. 2B. The cumulative indicator 122 is placed on the filter 14 near the bridge portion 20 of the trim 16 and includes a first patch 130A, second patch 130B, third patch 130C, fourth patch 130D, and fifth patch 130E arranged in a ring and in a clockwise order from the perspective of FIG. 2B. The first patch 130A through the fifth patch 130E are configured to visibly activate at progressively greater temperatures, indicated respectively by a first marker 134A, second marker 134B, third marker 134C, fourth marker 134D, and fifth marker 134E. The markers 134 and activation temperatures of the patches 130 can vary as described above with regard to the cumulative indicator 22 shown in FIG. 2A.

Figure 2C:
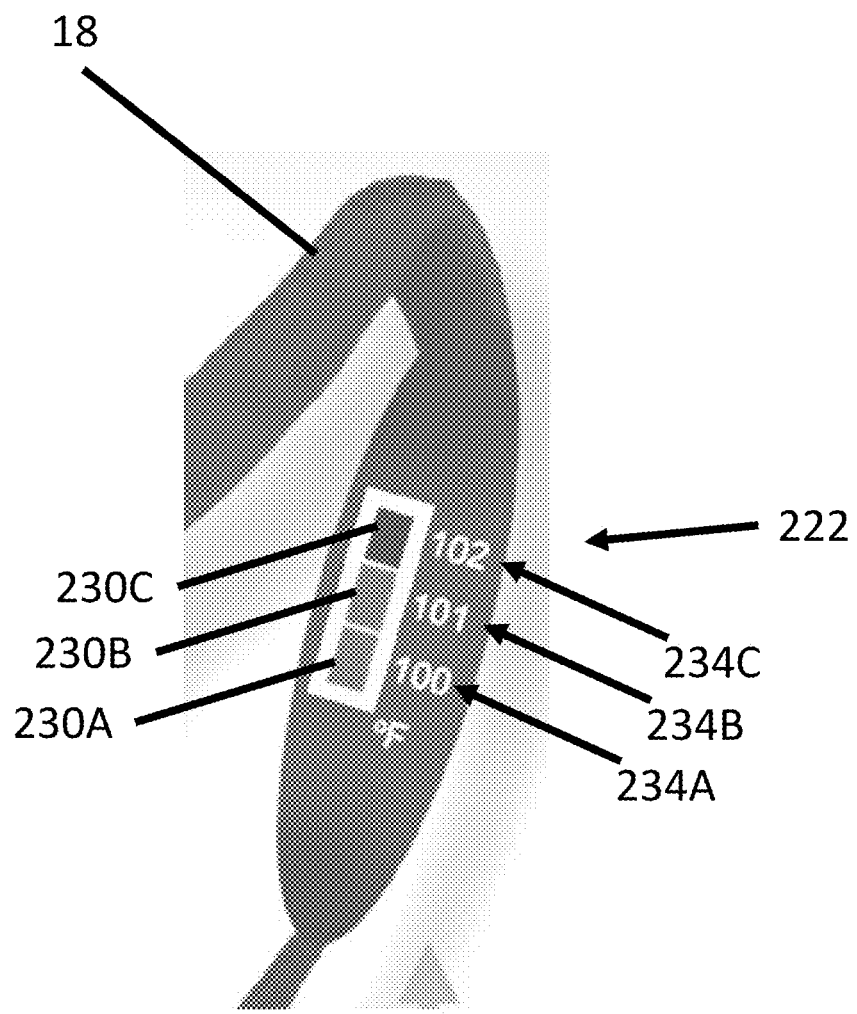

A cumulative indicator 222 according to a third arrangement is shown in FIG. 2C and includes a first patch 230A, second patch 230B, and third patch 230C configured to visibly activate at progressively greater temperatures indicated by a respective first marker 234A, second marker 234B, and third marker 234C. The patches 230 are arranged in a vertical row along the loop 18, from first patch 230A through the third patch 230C. The markers 234 and activation temperatures of the patches 230 can vary as described above with regard to the cumulative indicator 22 shown in FIG. 2A. The cumulative indicator 222 is attached to or integrated with one of the loops 18 at a location that will sit behind the wearer's ear when the mask 10 is worn. The cumulative indicator 222 is therefore more discrete than the indicators 22, 122 of FIGS. 2A and 2B because the location behind the ear makes the cumulative indicator 222 of FIG. 2C less visible to observers. The cumulative indicator 222 can be checked by the wearer by temporarily removing the loop 18 from behind the wearer's ear. The location behind the wearer's ear may also provide a more reliable transfer of heat from the wearer's body to the indicator 222.

Figure 2D:
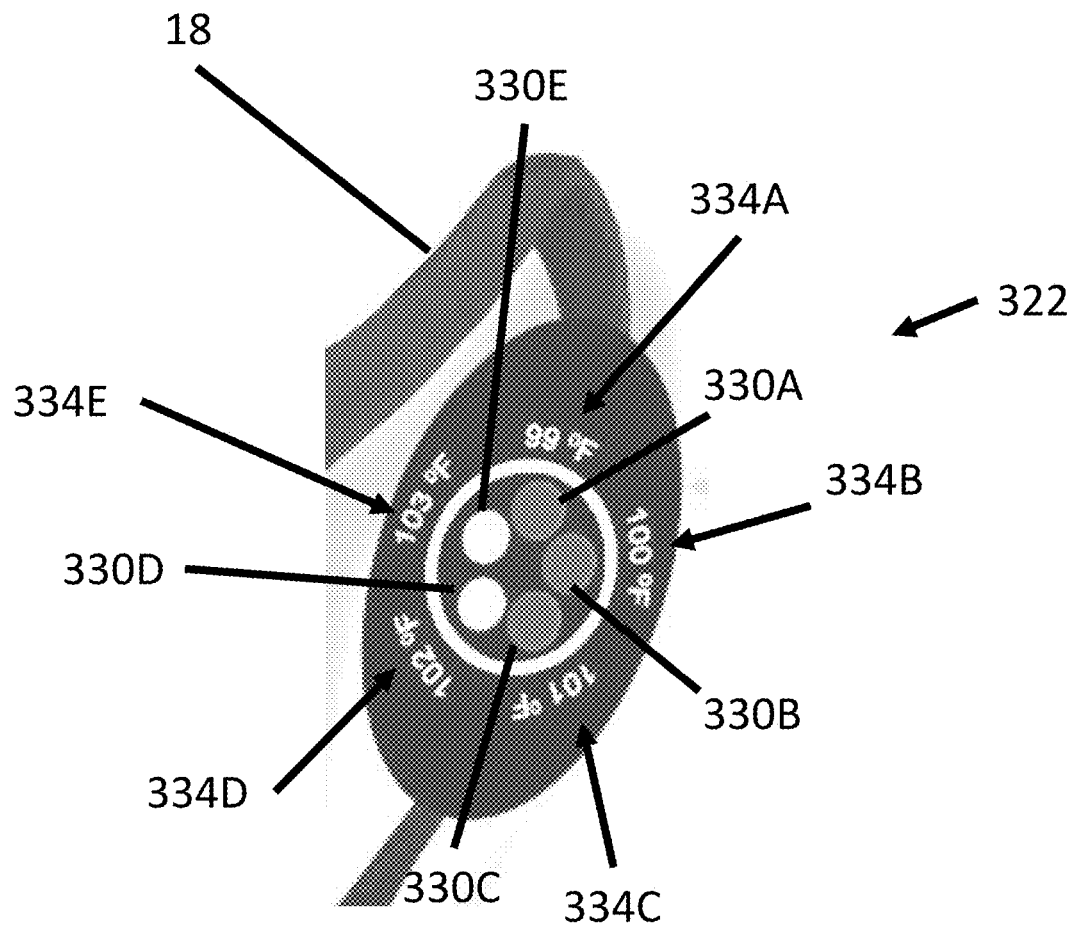

A cumulative indicator 322 according to a fourth arrangement is shown in FIG. 2D and includes a first patch 330A, second patch 330B, third patch 330C, fourth patch 330D, and fifth patch 330E configured to visibly activate at progressively greater temperatures indicated by a respective first marker 334A, second marker 334B, third marker 334C, fourth marker 334D, and fifth marker 334E. The markers 334 and activation temperatures of the patches 330 can vary as described above with regard to the cumulative indicator 22 shown in FIG. 2A. The patches 330 are arranged clockwise from the perspective of FIG. 2D from the first patch 330A through the fifth patch 330E. Like the cumulative indicator 222 of FIG. 2C, the cumulative indicator 322 of FIG. 2D is located on a loop 18 to sit behind the wearer's ear when the mask 10 is worn.

Figure 3A:
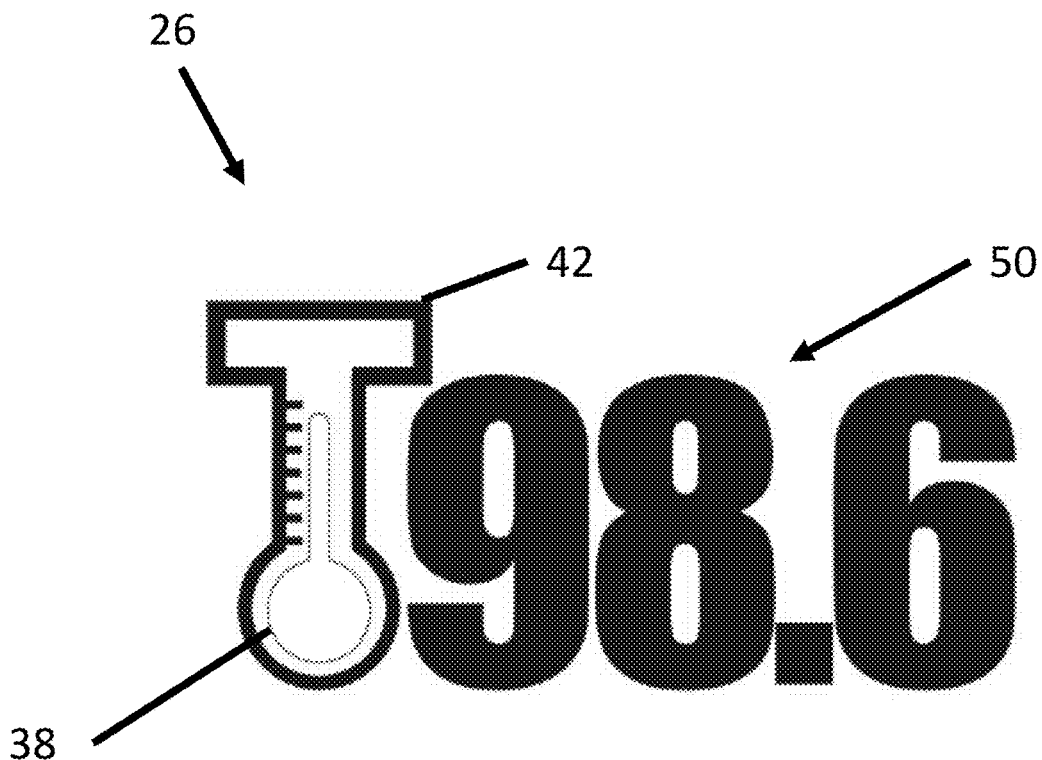
FIGS. 3A and 3B illustrate an interval temperature indicator for the mask of FIG. 1 in a unlit state and a lit state, respectively.
Figure 3B:
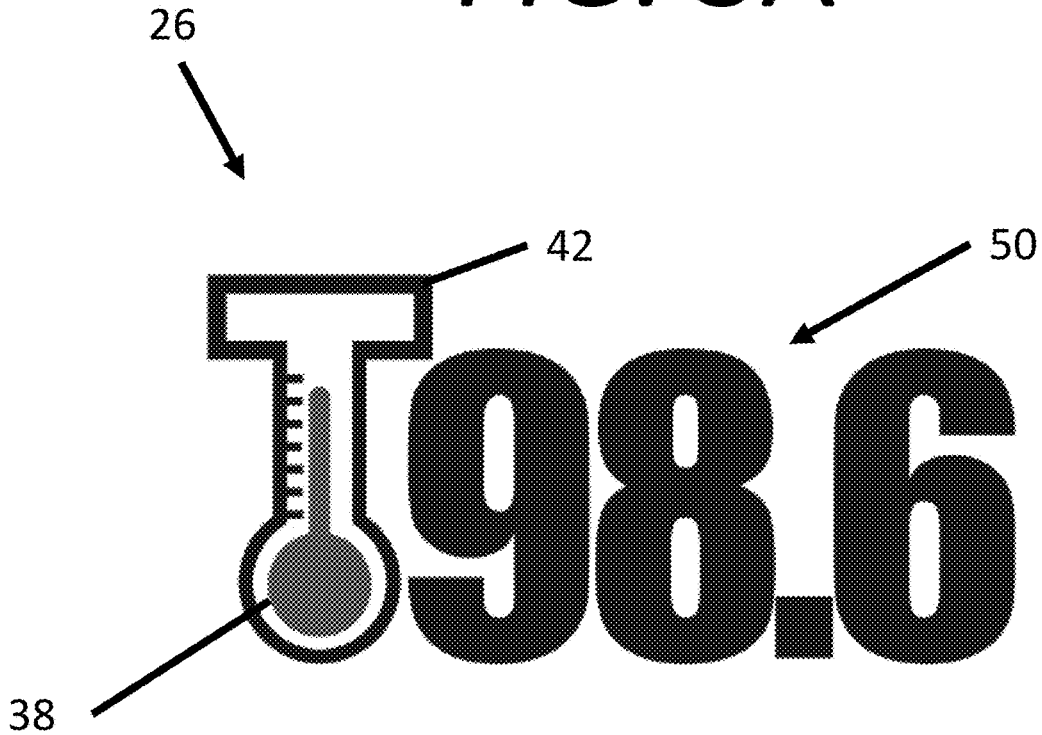

The interval indicator 26 is shown in an unlit and a lit state in FIGS. 3A and 3B, respectively. The interval indicator 26 of the illustrated example includes a lighting element 38 such as, for example, a light emitting diode (LED), a visible border 42 surrounding the lighting element 38, and a visible ornament 50 adjacent to the border 42. The border 42 serves to direct an observer's attention to where the lighting element 38 would be visible if lit.

In the illustrated example, the ornament 50 further serves to attract the observer's attention to the interval indicator 26 and to remind the observer of the average body temperature of a healthy human, thereby aiding the interpretation of the markers 30 of any of the cumulative indicators 22 described above. However, in alternative examples, the ornament 50 can be replaced by a digital display, such as a liquid crystal display (LCD), that can shows the wearer's body temperature. Such a digital display may be used instead of the cumulative indicator 22 and the rhythm indicator 26.

The lighting element 38 flashes or blinks in a rhythm that varies as a function of the wearer's temperature. Any function of the wearer's temperature can be used, and some examples are set out below.

In a binary function, the lighting element 38 may be configured simply to light if the wearer's temperature exceeds a threshold, such as a temperature above 100° F. or any other designated temperature.

In another function, the lighting element begins to blink when the wearer's body temperature exceeds a lower threshold. The blinking frequency may increase with increasing body temperature beyond the threshold. The blinking frequency may specifically correspond to an amount that the wearer's body temperature is below an upper threshold. Where an upper and lower threshold are both used, the upper threshold must be higher than the lower threshold.

In another function, the lighting element 38 switches between lit and unlit on an interval equaling one tenth of a second per tenth of a degree that the wearer's body temperature is below the upper threshold. To illustrate, where the upper threshold is 100° Fahrenheit, the interval is 1 second at 99° Fahrenheit and scales down to 0.1 second at 99.9° Fahrenheit.

In another function, the lighting element 38 blinks a number of times between pauses, with the number of blinks increasing as a function of the wearer's temperature above a threshold. The pauses may be any length of time from 0.5 through 6 seconds long, or specifically any half second or full second between 0.5 and 6 seconds long. The lighting element 38 may blink between pauses one time per degree Fahrenheit above a threshold. To illustrate, where the threshold is 100°, the lighting element 38 would blink once between pauses at 101°, twice between pauses at 102°, and so on. Alternatively, the number of blinks between pauses may be per half degree Fahrenheit or per half or quarter degree Celsius that the wearer's temperature rises above a threshold. The pauses between blinks may include a longer flash from the lighting element 38, which may last for any of the durations described above as exemplary durations for the pause. The pause may include a two second period where the lighting element 38 is unlit, and a two second period where the lighting element 38 is lit, in any order.

The above described lighting rhythm functions can be combined into a stepwise function, with different rhythms corresponding to different temperature ranges. In some such combinations, the lighting element 38 switches between lit and unlit on an interval of one tenth of a second per tenth of a degree that the wearer's temperature is below 100° Fahrenheit when the wearer's temperature is less than 100° and at least 99°, then blinks once per degree that the wearer's temperature exceeds 100° when the wearer's temperature is at least 100°.

Any of the temperature thresholds used in any of the above described functions may be any temperature from 94° through 106° Fahrenheit, or specifically any integer or half degree value in degrees Fahrenheit from 94° through 106° Fahrenheit, or any integer, half degree, or quarter degree value Celsius from 34° through 42° Celsius.

A circuit 54 for controlling a lighting element as may be used with the cumulative indicator 22 or interval indicator 26 described above is illustrated in FIG. 4A. The circuit 54 includes a thermistor 56 to measure the temperature of the wearer. The thermistor 56 of the illustrated example is coupled to a capacitor 57 such that the thermistor 56 and capacitor 57 cooperate to produce a waveform that varies as a function of the temperature of the thermistor 56. The circuit 54 includes an output 58 to selectively power the lighting element, a battery 60, and an on/off switch 62. The circuit 54 of the illustrated example also includes a microprocessor 64 configured to receive the temperature from the thermistor 56 and to control the output 58 accordingly. The microprocessor 64 is responsible for creating the above described lighting rhythms for the interval indicator 26.

The circuit 54, or specifically the microprocessor 64, is configured to adjust for an expected difference between the wearer's core body temperature and the actual temperature of the thermistor 56 or other temperature measuring device. In some examples, the mask 10 is provided with a calibration function so that the user can calibrate the circuit on their own body. Thus, the microprocessor 64 can control the output 58 appropriately for the wearer's body temperature despite differences between the actual temperature at the thermistor 56 and the wearer's core body temperature.

The circuit 54, or specifically the microprocessor 64, may have a battery conservation function. The battery conservation function varies the frequency at which the wearer's body temperature is measured while the switch 62 is in the on position. According to the function, the circuit 54 will wait for a long interval before checking temperature again after a normal body temperature is detected, and the circuit 54 will wait for a short interval before checking temperature again after an abnormal temperature is detected.

In some examples, when the circuit 54 detects a wearer's body temperature below a threshold, such as 100°, Fahrenheit, the circuit 54 will wait through a long interval, such as one minute, one half of an hour, or one hour, before checking the wearer's temperature again. If the circuit 54 detects the wearer's body temperature above the threshold, the circuit will only wait through a short interval, such as one second, 30 seconds, or 60 seconds, before checking the wearer's temperature again. The threshold can be any of the temperature thresholds described above with regard to the lighting rhythms of the interval indicator 26.

Figure 4A:
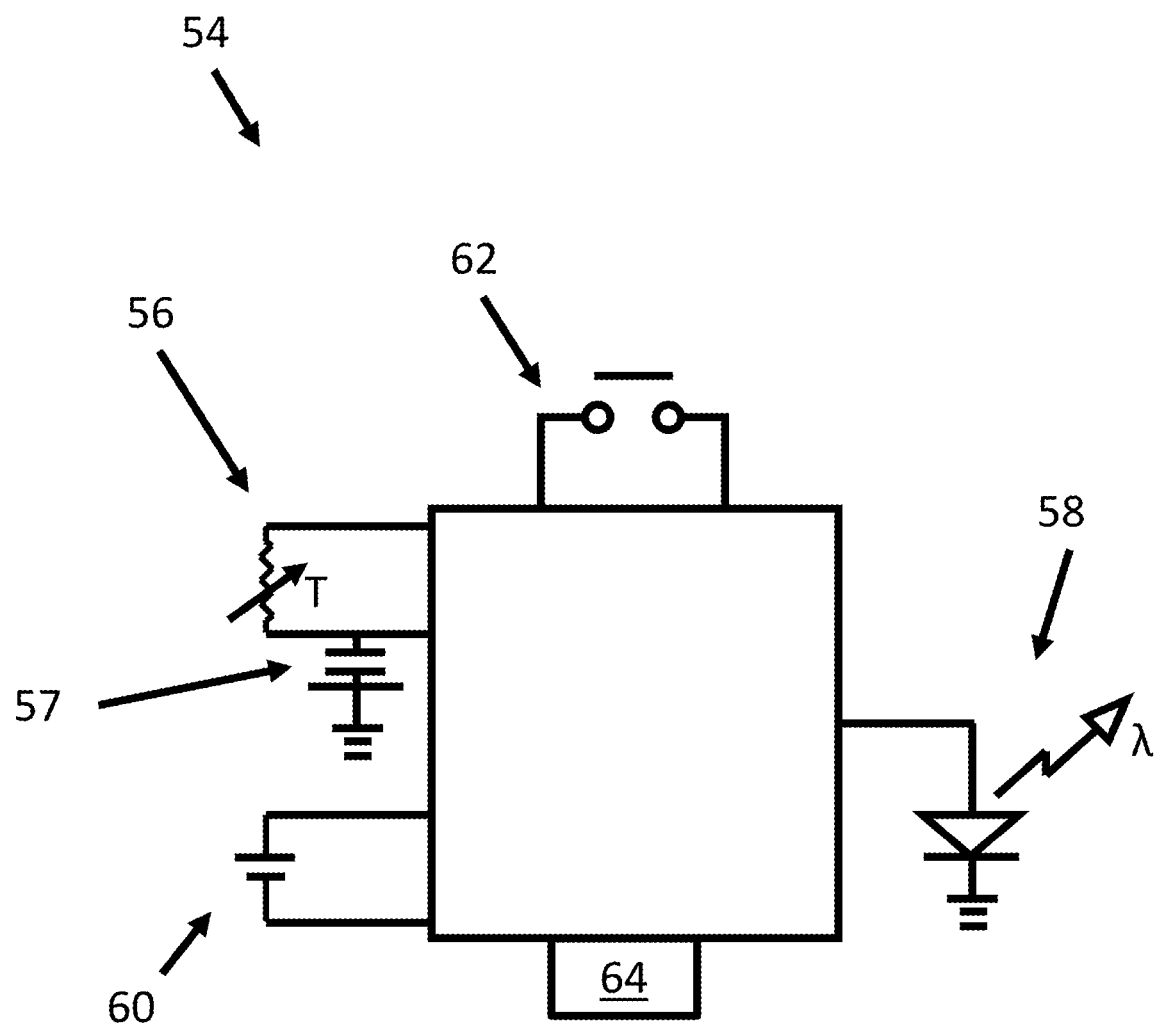
FIG. 4A illustrates a circuit for controlling a lighting element for use with the indicators of FIGS. 2A-3B.

The circuit 54 and its components may be located at any location on, within, or external to the mask 10. The thermistor 56 specifically may be located behind the wearer's ear, on the wearer's forehead, under the wearer's tongue, or on the wearer's cheek. Although the circuit 54 is illustrated in FIG. 4A with only one thermistor 56, multiple thermistors may be used.

Figure 4B:
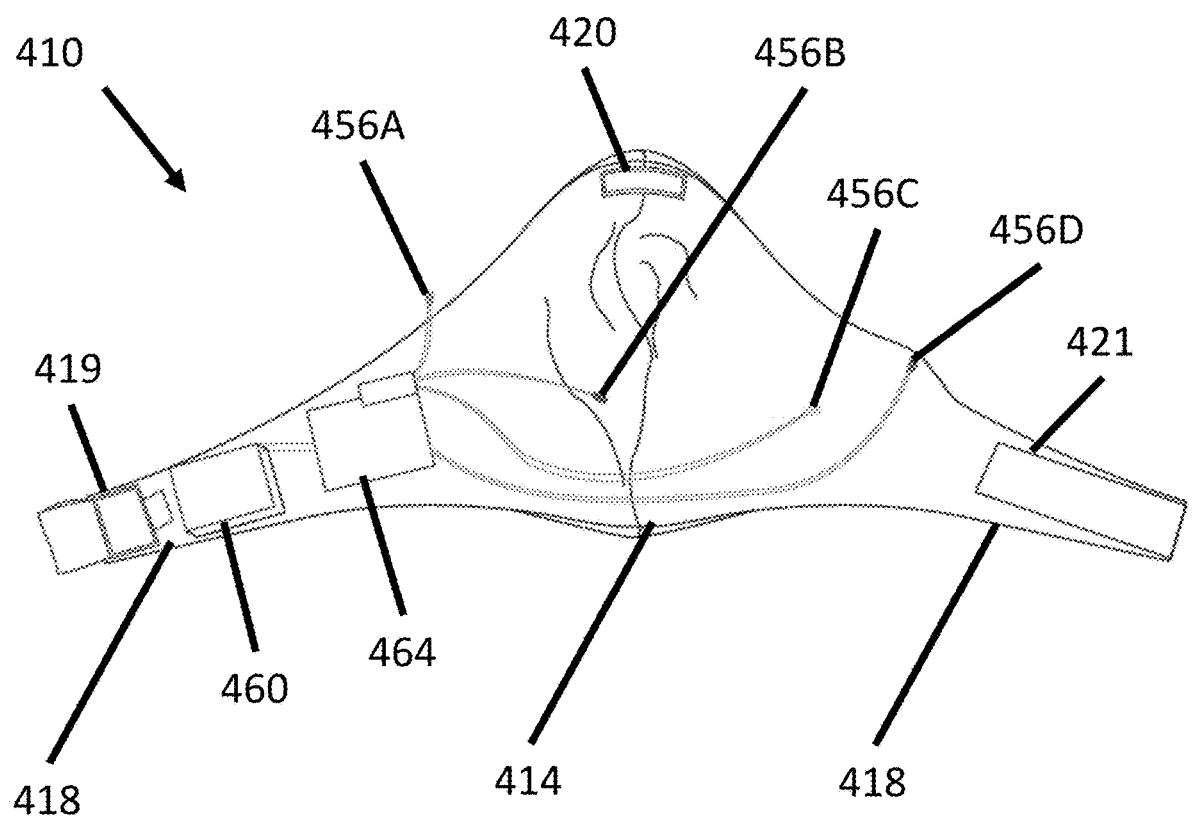
FIGS. 4B-4D illustrate an exemplary arrangement of circuit elements on a mask.
Figure 4C:
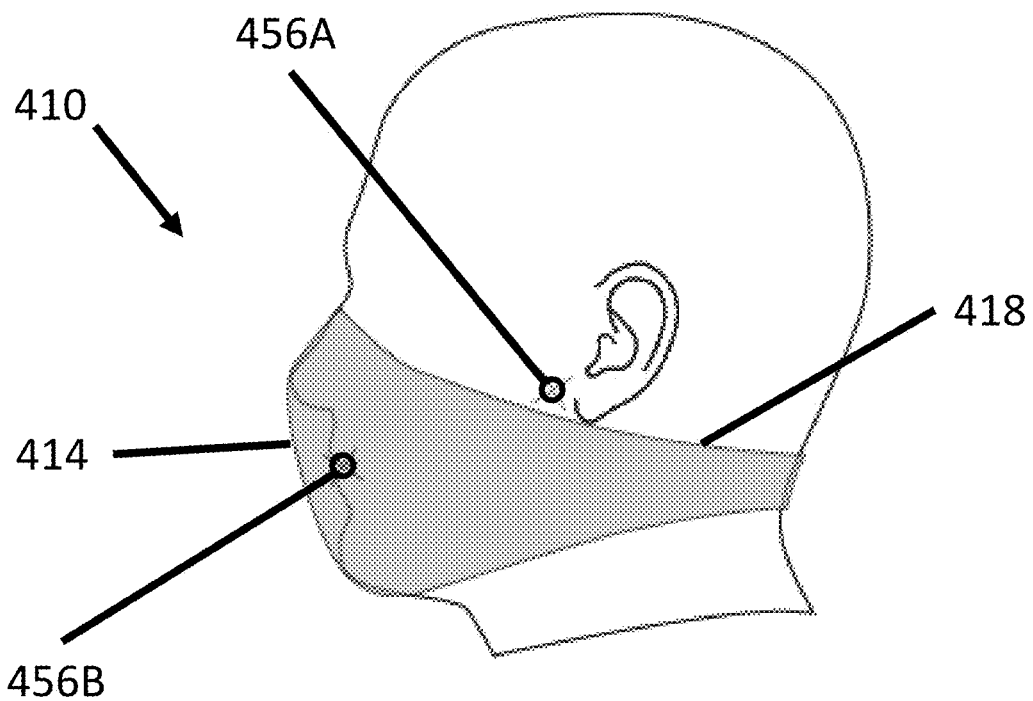
Figure 4D:
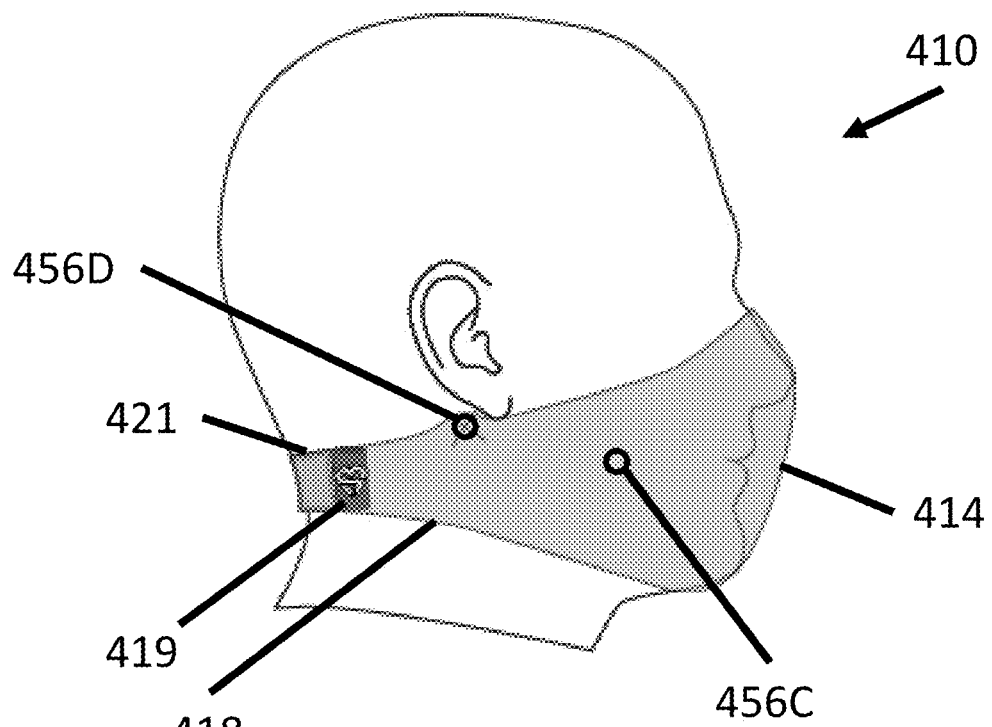

A particular arrangement of a battery 460, microprocessor 464, and multiple thermistors 456 is shown in FIGS. 4B-4D. A mask 410 includes two lateral wings 418 on either side of a filter 414 and bridge element 420, with one lateral wing 418 ending in a buckle 419 and the other lateral wing ending in a strap 421 retainable by the buckle 419. The battery 460 and microprocessor 464 are placed on one of the straps 418, and four thermistors extend from a connection point near the microprocessor 464. A first thermistor 456A exits the mask 410 near the wearer's cheek to measure ambient temperature. A second thermistor 456b extends into the wearer's mouth and possibly under the wearer's tongue to provide a first measure of the wearer's body temperature. A third thermistor 456C and a fourth thermistor 456D sit on the wearer's cheek and behind the wearer's ear beneath the mask, respectively, to provide respective second and third measures of the wearer's body temperature. The third thermistor 456C may specifically be located directly on the skin over the wearer's auricular artery. The microprocessor 464 is programmed to interpret the first, second, and third measures of the wearer's body temperature in view of the ambient temperature to arrive at an accurate estimate of the wearer's true body temperature. In alternative arrangements, a location for a fifth thermistor, or an alternative location for one of the first, second, third, and fourth thermistors, may be on the wearer's forehead, or specifically on the wearer's skin directly above the wearer's temporal artery, with the microprocessor 464 programmed to take that location into account. The foregoing aspects of the mask 410 of FIGS. 4B-4D can be combined or interchanged in any manner with the features of the mask 10 of FIG. 1. Further, although a thermistor is a suitable temperature measuring device, any temperature measuring device with a digitizable output may be used instead of a thermistor in any of the foregoing examples.

Figure 5A:
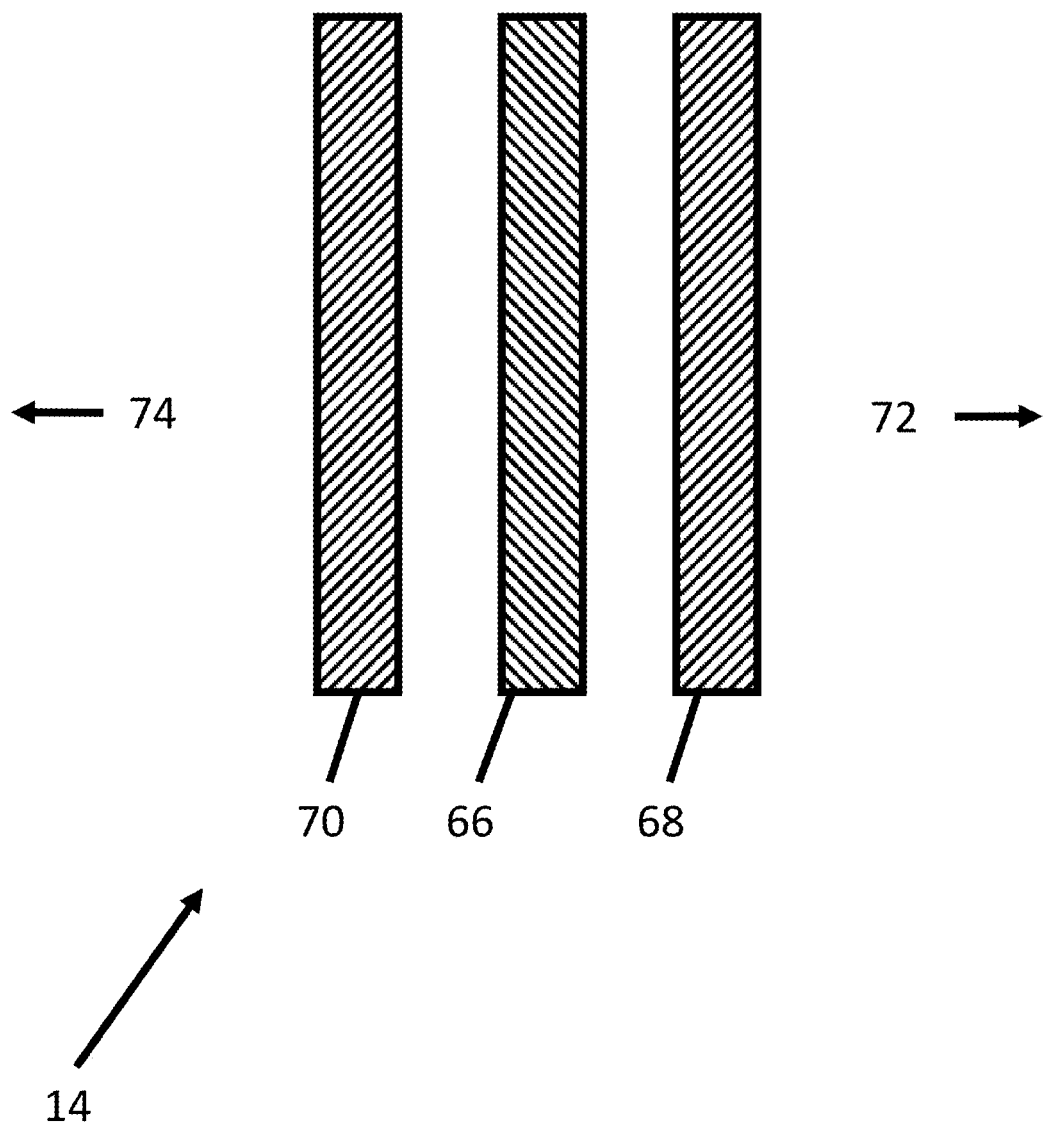
FIG. 5A is a cross-sectional view of a portion of a filter of the mask of FIG. 1 according to an arrangement.

A portion of the filter 14 according to an arrangement is shown in cross-section in FIG. 5A. The filter 14 of the illustrated example includes an antiviral layer 66, an inner layer 68, and an outer layer 70. The inner layer 68 is positioned in an inward direction 72, which is toward the wearer when the mask 10 is worn as intended, relative to the antiviral layer 66. Similarly, the outer layer 70 is position in an outward direction 74, which is away from the wearer when the mask 10 is worn as intended, relative to the antiviral layer 66. Features of the cumulative indicator 22 and interval indicator 26, including the markers 34, border 42, ornament 50, and the thermochromic ink of the patches 30 are printed on the outer layer 70. The lighting element 38 is placed between the outer layer 70 and the antiviral layer 66 behind the border 42.

The inner layer 68 and outer layer 70 may be of any suitable substance or construction, such as a fabric, including fiber mesh, or porous polymer. In accordance with the present disclosure, the term "fabric" refers to woven, non-woven, and knit materials. Contemplated non-woven fabrics include spunbound or spunlace, airlaid, drylaid, and wetlaid fabrics. The antiviral layer 66 includes an actively antiviral substance. In some examples, the antiviral substance is copper. A fabric including copper fibers is within the scope of the disclosure. An example embodiment of the antiviral layer includes a fabric dip-coated in copper. The dip-coated fabric may comprise cotton, polyester, lycra, or any other air-permeable material. In other arrangements, copper or another antiviral substance is printed or sprayed on either or both of an outward facing side and an inward facing side of the antiviral layer 66. Any one of or any combination of the antiviral layer 66, inner layer 68, and outer layer 70 may be constructed of a non-woven material such as that used in known N95 or K2 masks.

Figure 5B:
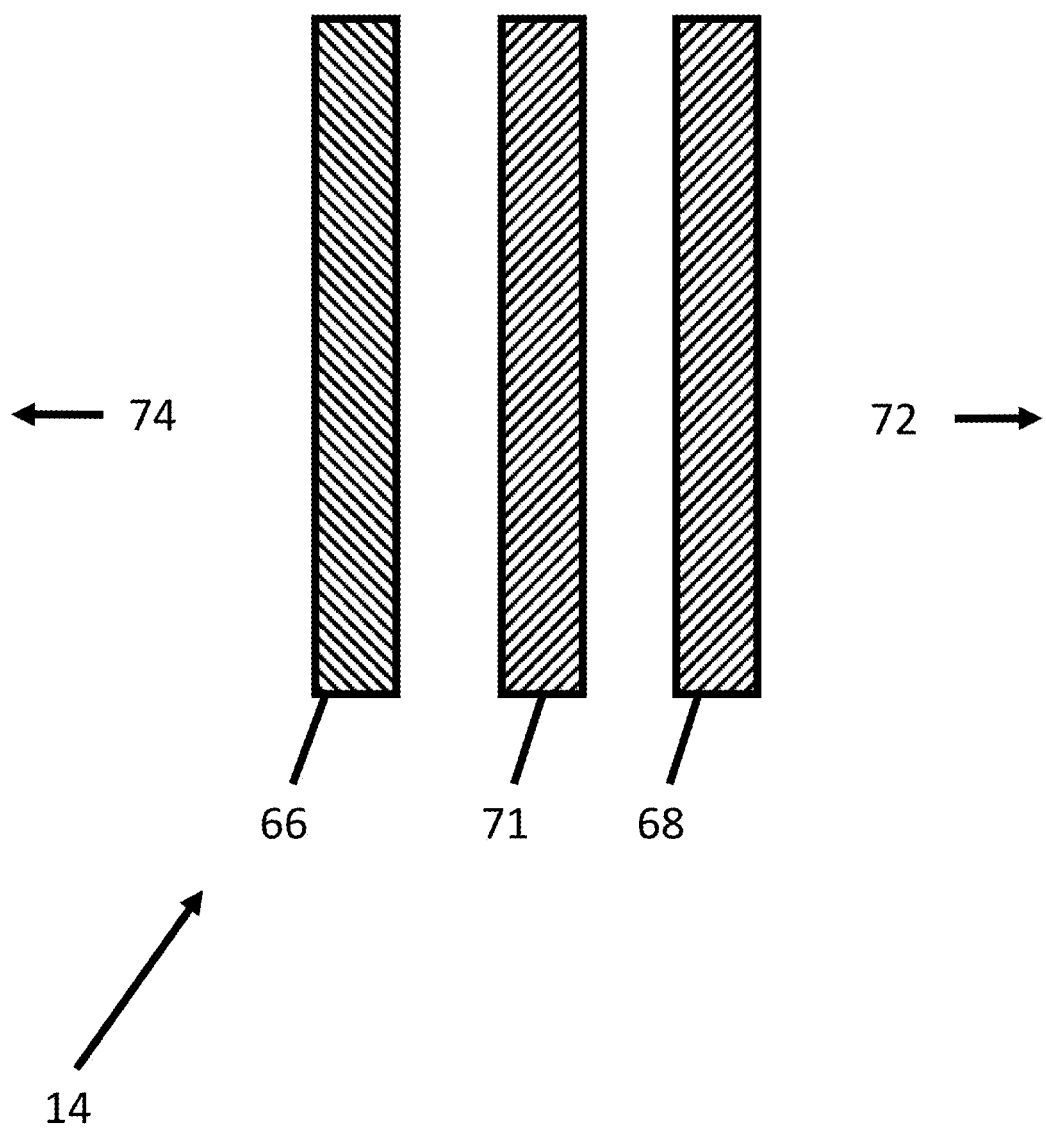
FIG. 5B is a cross-sectional view of a portion of the filter of the mask of FIG. 1 according to another arrangement.

Another arrangement of the filter 14 is shown in FIG. 5B. In the arrangement of FIG. 5B, the antiviral layer 66 is the layer of the filter 14 furthest in the outward direction 74. Positioning the antiviral layer 66 to provide the outward-facing surface of the filter 14 reduces risk of contamination of the filter 14 such as when the user touches the filter 14 or sets the mask 10 down. An uncoated middle layer 71 exists between the inner layer 68 and the antiviral layer 66 in the arrangement of FIG. 5B. This middle layer 71, or both the middle layer 71 and the inner layer 68, may be excluded in some alternative arrangements of the mask.

Exemplary antiviral coatings as may be applied by, for example, dip coating, spraying, or printing to an article, such as the antiviral layer 66, an HVAC filter, a garment, bedding, or any other article that may benefit from antiviral treatment, with mixtures including particles of a metal or metal oxide having antiviral properties, such as copper, silver zinc, gold, copper oxide, silver oxide, zinc oxide, and/or gold oxide, one or more essential oils, a binder, and an emulsifier. Exemplary binders include resinous binders, such as acrylic, epoxy, pine tar, and coal tar, though most thermosets and thermoplastics and, more generally, most organic and synthetic resins may be used. The mixture may further include additional metal or mineral based antiviral agents, such as titanium dioxide or other metal oxides. The metal, mineral, and metal or mineral based ingredients may be present in microparticles or colloidal suspension, with specific examples including copper microparticles and colloidal silver. The particles of antiviral or generally antimicrobial metal, metal oxide, or mineral may be on a micron-scale, meaning they may have diameters generally distributed between 1 micron and 10 microns, or between 1 micron and 20 microns, or diameters of equal to or about 1, 2, 3, 4, 5, 6, 7, 8, 9, or 10 microns. The immediately foregoing examples of metal or metal oxide particle sizes are particularly suitable for breathing masks, but broader ranges of particle sizes may be useful for other applications, such as HVAC filters. Nanoparticles of the foregoing metals or metal oxide are therefore contemplated as ingredients of mixtures according to some examples, and particles having diameters generally distributed in the ranges of from 1 micron to 100 microns, 1 micron to 200 microns, and 100 microns to 200 microns may be used mixtures according to other examples. Alternatively, in mixtures with sufficient concentrations of antiviral oils or other antiviral compounds, metal and metal oxides may be omitted altogether.

The one or more essential oils may be any one or any combination of oils chosen for their aroma or antiviral properties. Suitable essential oils include, for example cinnamon oil, tea tree oil, eucalyptus oil, thyme oil, clove oil, orange oil, carrot seed oil, lemongrass oil, perilla oil, peppermint oil, coriander oil, lavender oil, rosemary oil, citron oil, blumea oil, and propolis oil. Contemplated oil components of the mixture include any one or any combination of the foregoing oils, or any one or any combination of any subset thereof. Any other essential oils may be included in addition to or instead of the foregoing oils and mixtures thereof in any combination to achieve a desired aroma and degree of antiviral activity. In alternative mixtures, some or all of the essential oil may be replaced with extracts, synthetic oils, or other substances including the same or similar active ingredients to the essential oils listed above.

The emulsifier is present in a relatively low quantity within the mixture in proportion to the essential oils such that the essential oils mix impermanently with the water-dissolved binder, forming an emulsion of low stability and resulting in slow release of the essential oils from the coating after the coating is applied to the antiviral layer. For example, during mixing of the ingredients prior to application thereof to the article or fabric, binder resin, such as acrylic, may be mixed into an emulsion containing water, the oil, antiviral or generally antimicrobial particles of metal or metal oxide, such as copper or copper oxide, and an emulsifier, such as tween. Hot melt adhesive, such as a resin of different type than the binder resin, may also be within the emulsion. The coating, after it is cured and in solid form upon the antiviral layer, therefore includes the oil dispersed in an unstable suspension within the solidified resin. The instability of the suspension causes the coating to gradually release the oil. The reference to an unstable suspension here therefore means that the oil within the solidified coating will gradually separate from the coating and move, migrate, or bloom to the surface of the coating rather than remaining permanently integrated therein. Exemplary emulsifiers for this purpose include polysorbates, such as polysorbate 80 (or "tween"). Tween, however, could be substituted with any other non-toxic emulsifier. The gradual release of the essential oils creates a film on the surface of the coating. With certain antiviral essential oil formulations, the film enhances the on-contact antiviral properties of the coating. Depending on the formulation, the film may create a vapor that acts to inhibit viruses present in air or on nearby surfaces, including the airways of the wearer of the mask.

Including a humectant in the mixture can reduce the amount of essential oil dried from the coating as it is cured upon the antiviral layer 66, and the release rate of the essential oil after the coating is cured can be controlled by adjusting the concentration of the humectant within the mixture to improve the release rate of the oil. The humectant or humectants, if included, would provide differing amounts of the mixture depending on the type of humectant or humectants used. Where the humectant is propylene glycol, the humectant component of the wet, pre-curing state of the mixture can be about 1%, about 2%, anywhere from 0% to about 3%, or from 1% to 3% of the mixture by weight. In other example, the humectant component of the wet, pre-curing state of the mixture could be up to up to 30% of the mixture by weight. Humectants with intrinsic antiviral properties, such as propylene glycol, can improve the overall antiviral efficacy of the coating. Propylene glycol, and other humectants with similar evaporative properties, have the further benefit of facilitating the airborne dispersion of the essential oils.

The release rate of the oils from the coating may also be controlled by adjusting the cure parameters. Either or both of the time and temperature of the curing process may be relatively low such that the binder is not cross-linked. The coating is cured until enough water evaporates from the moisture such that the binder may solidified upon the fabric immediately or after cooling to room temperature, referring here to any temperature between 60° F. and 100° F., but the curing stops without any cross-linking within the binder. As appropriate for a given fabric, the mixture may be applied to the sheet for the antiviral layer by any application process such as rotary screen, flat screen, knife coat, reverse roll coat, slot die, flexo, gravure, offset, immersion coating, air knife, knife over roll, spray, hot laminating or hot pressing, cold laminating, and pad printing. The mixture may be applied with or without any curing step prior to application. That is, the mixture may be kept below curing temperature, such as below about 40° or about 45° Fahrenheit, at all times between mixing the ingredients of the mixture together and application of the mixture to the fabric. After the mixture is so applied, the mixture is partially cured such as by heating the sheet at 105° to 135° degrees Fahrenheit for two to four minutes, or at 260° to 300° for 45 to 90 seconds, or combinations of heat and duration between those extremes that would result in similar outcomes. Partial curing here refers to withdrawal of the coated article from the elevated curing temperature early enough to prevent the resin binder from cross-linking at all, but after the resin binder is solidified. Specific examples include heating the sheet at 120° Fahrenheit for three minutes or heating the sheet at 280° Fahrenheit for one minute. In particular, it is noted that the hot-curing can be conducted at temperatures above or below the boiling temperature of water.

The coating may act as an adhesive between the antiviral layer 66 of a mask and either or both of an inner layer 68 and an outer layer 70. For example, the mixture may be applied to the antiviral layer 66, and either or both of the inner layer 68 and outer layer 70 may be set into place upon the antiviral layer 66. The layers may then be heated according to any of the foregoing curing processes, with hot pressing being one specific suitable example. The coating may also act as an adhesive between the antiviral layer 66, or the filter 14 generally, and the loops 18.

The curing time and temperature may be selected in view of the oil blend to achieve an intended scent profile. Aromatic fractions in antimicrobial some essential oils, including some of those listed above by way of example, have a lower flash point than the compounds providing the oils with their antimicrobial, or specifically antiviral, properties, specifically, eugenol and phenol. In particular, the flash point of phenol is 174° F., and the flash point of eugenol is 219°. It is therefore possible to reduce or remove the scent of an essential oil while preserving its antimicrobial or antiviral properties by heating the oil, or a mixture containing the oil, to a maximum temperature above the flashpoint of the undesired aromatic fraction but below the flashpoint of the desired antimicrobial or antiviral compounds. Propylene glycol, another exemplary antimicrobial or antiviral ingredient for the mixture, has a flash point of 213° F., and will therefore also remain in the mixture at temperatures that would burn off certain aromatic fractions.

Because flashpoints also differ between specific aromatic chemicals, it is possible to burn off the aromatic fraction of certain oils while preserving the aromatic fraction of other oils. For example, the flashpoint of the aromatic fraction of eucalyptus oil is 116° F., and the flash points for the aromatic fractions of certain other oils are 131° F. for thyme oil, 147° F. for tea tree oil, 197° F. for cinnamon oil, and 200° F. for clove oil. Heating a blend of essential oils to a temperature above the flashpoint of a first aromatic chemical or fraction contained therein, but below the flashpoint of a second aromatic chemical or fraction contained therein, will cause only the second aromatic chemical or fraction to remain. The oil blend thus heated will only have the scent of the second aromatic chemical or fraction. For example, a blend of eucalyptus and tea tree oils may be heated until the aromatic fraction of the eucalyptus oil begin to burn, or to at least 116° F., or any temperature between 116° F. and 147° F. The mixture containing the eucalyptus and tea tree oils is then removed from heat and cooled before the temperature of the mixture rises to 147° F. This process removes some or all of the aromatic fraction within the eucalyptus oil while preserving the aromatic fraction and scent of the tea tree oil and the antimicrobial, or specifically antiviral, properties of the blend. Effective temperatures for burning off certain scents while retaining others in the same manner as this example can be derived in view of the above listed flashpoints as well as those discovered or known for the aromatic fraction of any other oil. Generally, where an undesired fraction has a lower flashpoint temperature than a that of a desired fraction, the undesired fraction can be burned off and the desired fraction can be preserved by selecting curing temperature and duration such that the mixture reaches a maximum temperature during the curing process that is between the flashpoint of the undesired fraction and the flashpoint of the desired fraction.

It can be useful to control the aroma of the essential oil blend because the coating described herein is formulated and treated in a manner that may produce an end product that exudes the oil blend as an antimicrobial, or specifically antiviral, vapor into the surrounding air. In the specific example of a face mask, the oil blend may thus kill microbes, and specifically viruses, within the mouth, nose, and throat of the wearer. The scent of any aromatic fraction remaining in the cured coating will therefore be quite evident to the user of any coated product.

The mixture may also be formulated and heated to result in a desired ratio of antimicrobial compounds. The most effective ratio of antimicrobial compounds varies between types of microbes, and even between viruses. Thus, the formula and curing process of the coating may be adjusted to target a certain microbe or a certain group of microbes, or more specifically a certain virus or group of viruses. The effectiveness of the phenol to eugenol ratio may be balanced against the desirability of the scent profile when formulating an essential oil mixture. Essential oils containing aromatic fractions that burn at relatively low temperatures may be added to adjust the phenol to eugenol ratio without leaving any detectable scent on the end product. Isolated terpenes may also be added for the same purpose. Some or all phenol may also be burned off during the curing process by heating the coating to a maximum temperature equal to or above 174° F.

Effective formulations for the mixture vary depending on the substances selected for each role. However, generally, the mixture is one to two thirds, inclusive, or in a more specific example 45% to 50%, water by weight. In various further examples, the mixture may be no more than two thirds, 60%, 50%, 45%, or 40% water by weight. The binder is 10% to 20% of the mixture by weight. The proportions of essential oils to metals and metal oxides in the mask may vary. Mixtures of at least 3% metal or metal oxide by weight and at least 6%, or from 6% to 12% inclusive, antiviral essential oil by weight are contemplated. Alternative examples include mixtures including at least 6% antiviral metal or metal oxide with no antiviral oils, or at least 12% antiviral essential oils with no antiviral metals or metal oxides. Emulsifiers may be 0.1% to 0.2% of the mixture by weight for relatively fast release of oil, but may be equal to or about 0.5% of the mixture for a slower release of oil, or a non-zero quantity of up to 2% of the mixture by weight for significantly slowed release of oil or where a large quantity of oil is used. Emulsifier may be included in the mixture at 0.1% to 2% of the mixture by weight before the mixture is cured, or may be provided in a lower quantity such that the emulsifier provides 0.1% to 2% of the coating by weight after the coating is cured. However, depending on what type of emulsifier is used, the emulsifier could provide, for example, up to 10% or up to 20% of the mixture by weight. The remainder of the mixture can be provided by any combination of fillers, thickeners, herbal extracts, or adhesives. In some examples according to any of the foregoing, the mixture specifically lacks any cross-linking catalyst.

Woven and non-woven fabrics may be coated with generally similar mixtures. Applications wherein another layer of material is to be adhered to the coated article, such as the filter 14 construction of FIG. 5A or 5B, may benefit from the addition of a hot melt adhesive. The hot melt adhesive may be a thermoplastic resin, with specific examples including copolyester, copolyamide, or any other thermoplastic crystalline hot-melts. The hot melt adhesive may be a different type of resin than the binder. An exemplary mixture composition for a fabric to be adhered to another layer of material includes, by weight, equal to or about 45% water, about 15% resinous binder, about 10% essential oil, about 0.5% emulsifier, about 4% antiviral metal, metal oxide, or mineral, and about 20% hot melt adhesive, with the remaining about 5.5% being fillers, thickeners, or herbal extracts, and with "about" referring to exactly the stated value or values greater or lesser than the stated values by up to one tenth.

Where the coated article does not need to be adhered to another layer of material, such as in HVAC filters or single layer textiles, the adhesive may be omitted. A formula without a dedicated adhesive may be derived by omitting the hot melt adhesive from the foregoing example and increasing the share of the remaining components to maintain their proportions relative to one another, such as by adding about one quarter more of each of the remaining components. Such a mixture would be about 56.25% water, about 18.75% resinous binder, about 12.5% essential oil, about 0.625% emulsifier, and about 5% antiviral metal, metal oxide, or mineral, with the remaining about 6.875% being fillers, thickeners, or herbal extracts.

After curing, the coating is free, or substantially free, of water. Example post-curing weight percentages for non-water ingredients may thus be derived mathematically by removing the water component from the above disclosed examples, or approximated by simply doubling any of the above disclosed weight percentages for non-water ingredients. Cured coatings including any weight percentages thus derived or approximated are contemplated. For example, the 6% to 12% oil by weight of the pre-cure mixture noted above indicates 12% to 24% oil by weight in the post-cure coating is contemplated.

The above described coatings may be applied to any fabric at a density per unit area that yields a desirable texture and degree of antimicrobial potency. In the example of facemasks similar in construction to those illustrated and described here, the coating may be applied to an antimicrobial or antiviral layer 66 in an amount resulting in a dried, post-cure mass of anywhere from 0.1 to 1 gram, or equal to or about half a gram, of coating per square inch of fabric, in some examples totaling to from 2 to 3 grams of dried coating in an entire mask of typical size.

Masks including a layer having the antiviral, or generally antibacterial, coatings described above may exist with or without any of the temperature indicating or temperature measuring features described elsewhere in this disclosure.

Alternative arrangements of the mask 10 lack either or both of the inner layer 68 and outer layer. In some examples, the mask 10 has no inner layer 68, and copper or another antiviral substance is printed or sprayed on the outward facing side of the antiviral layer 66, such that the inward facing side of the antiviral layer 66 is free of the substance or coating. In further examples, the mask 10 has no outer layer 70, and copper or another antiviral substance is printed or sprayed on either or both of the inward facing side and the outward facing side of the antiviral layer. In some arrangements, including, but not limited to, those wherein the antiviral layer 66 is the innermost layer of the filter 14, meaning the antiviral layer 66 contacts the wearer's face, the antiviral layer 66 may include uncoated regions free of the substance or coating. The uncoated regions may be at upper and/or lower edges of the antiviral layer 66. An uncoated region at the upper edge may, for example, be at the bridge portion 20, or along the entire upper edge, and an uncoated region at the lower edge may, for example, be a centered patch, or may extend along the entire lower edge. The uncoated regions may be on one or both sides of the antiviral layer 66. The uncoated regions serve, generally, to reduce or eliminate direct contact between the antiviral or generally antibacterial coating or substance on the antiviral layer 66 and the wearer's skin. This reduces undesired abrasion or transfer of oil from the coating to the skin.

The mask 10 may include further features and functionalities not specifically tied to structures illustrated in the figures. For example, the mask 10 may include a wireless communication feature such as an RFID element, possibly in communication with the microprocessor, that may communicate temperature data to a remote server or database for analysis. Further, the mask 10 may include a heating element for self-sterilization. The heating element may also be connected to the microprocessor 64. The heating element may be configured with a sterilization routine, such as raising the mask above a target temperature, such as 135° or 155° Fahrenheit, for a duration of time, such as half an hour, to sterilize the mask.

The foregoing describes certain illustrated arrangements of the mask 10, but several aspects of the mask may be varied individually or in combination in various alternative arrangements. In contrast to the mask 10 illustrated in FIG. 1, masks in various other arrangements may have an inflexible filter 14, lack a trim 16, lack a bridge portion 20, or any combination of the foregoing. Masks according to alternative arrangements may have a bandanna like structure to be tied around the wearer's head, or may include adhesive portions for adhering to the wearer's face instead of loops 18. In other arrangements, masks may be integrated with or connectable to hats or caps for the wearer's head. Masks in any arrangement may be designed either to be disposable or reusable.

Masks in various alternative arrangements include any one or any combination of the temperature indicating features described above. Specifically, masks may include any one of or any combination of the cumulative indicators 22, 122, 222, 322, interval indicator 26, a digital display, such as an LCD, and an analog thermometer, any of which will change appearance as a function of temperature. Such indicating features, individually or in any combination, may be used with or without an antiviral layer 66 in the filter 14. In other examples, the filter 14 lacks either or both of the inner layer 68 and outer layer 70.

The cumulative indicator 22 is integrated into the trim 14 over the bridge portion 20 of the illustrated example, but in other examples the cumulative indicator 22 is directly on the filter 14 or on the loops 18. Likewise, the interval indicator 26 of the illustrated example is located directly on the filter 14, but in other examples is located elsewhere on the filter 14, or is integrated into the trim 16 or a loop 18. Further, interval indicators 26 in alternative arrangements lack either or both of the border 42 and the ornament 50.

In further alternative arrangements, the markers 34 of any type of cumulative indicator 22, 122, 222, 322 may be presented in degrees Celsius, or may convey safety or a warning symbolically or through printed words. In further examples, the cumulative indicator 22 may include fewer markers 34 than patches 30, such as one marker 34 each an upper temperature and a lower temperature to enable observers to infer the meaning of patches 30 without a corresponding marker 34.

Any of the cumulative indicators 22, 122, 222, 322 can be varied to contain a differing number and arrangement of patches and markers. In some examples, cumulative indicators include as little as one patch with no marker to indicate when the wearer's body temperature exceeds a certain threshold. In further examples, the patches are of any shape or design, and are of differing shapes within a single cumulative indicator.

Figure 6A:
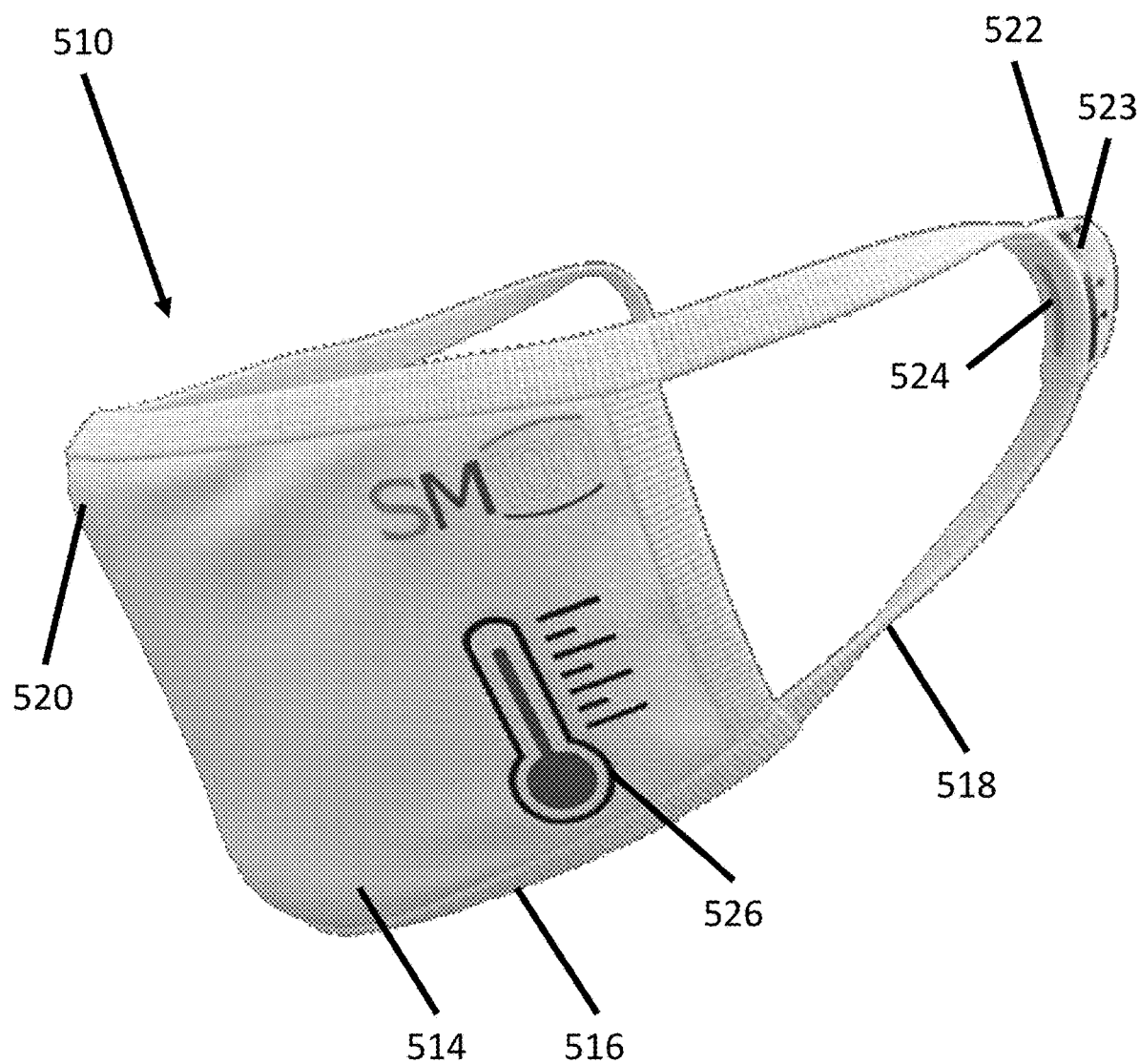
FIG. 6A is a perspective view of a breathing mask according to an alternative arrangement.
Figure 6B:
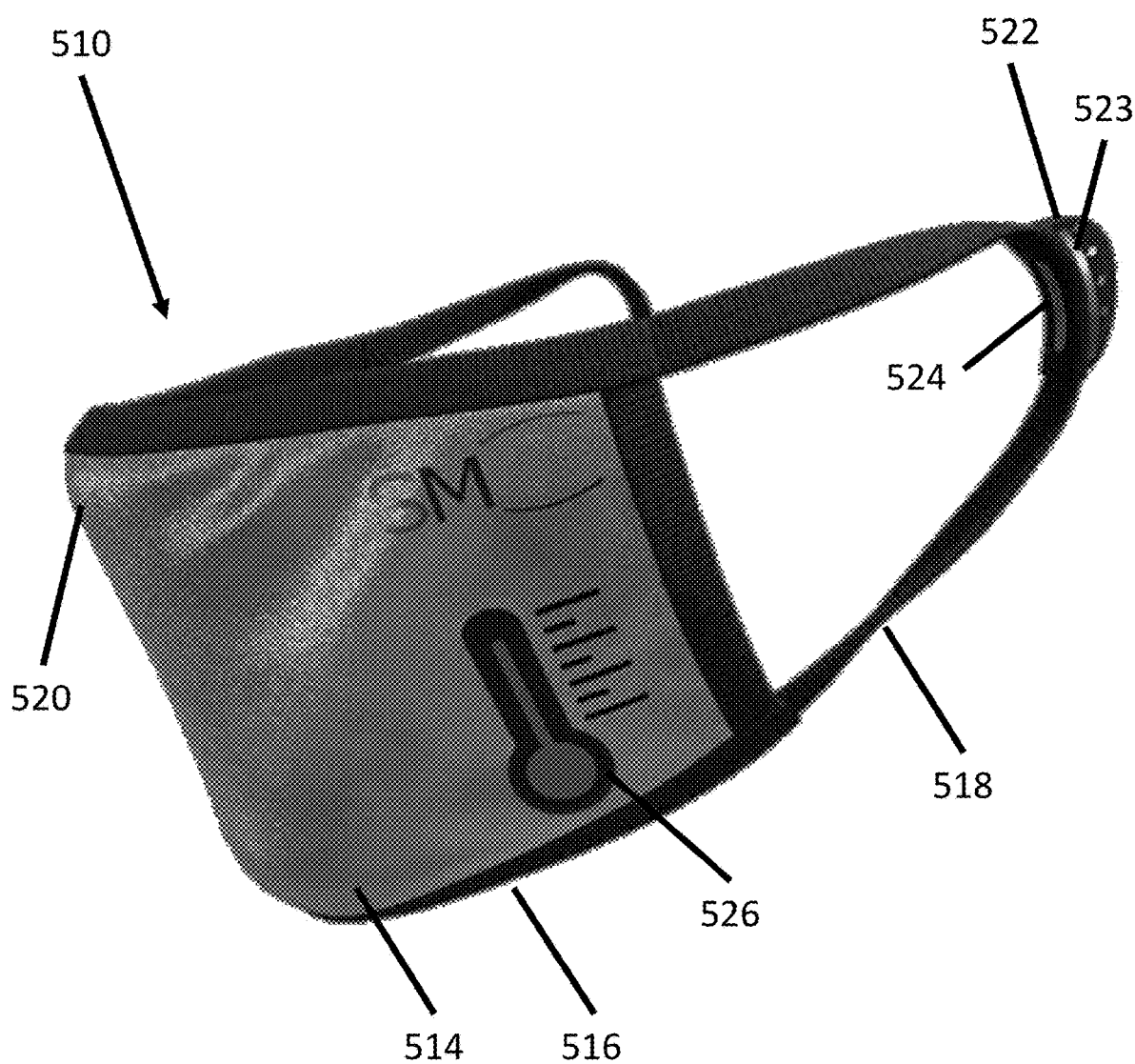
FIG. 6B is a perspective view of the breathing mask of FIG. 6A with a metallic coating on an outer surface of a filter.

FIGS. 6A and 6B illustrate a mask 510 according to an alternative arrangement showing exemplary recombinations of the above described features. The mask 510 includes a filter 514, trim 516, loops 518, and bridge portion 520, generally as described with regard to like features of the mask 10 of FIG. 1. Further, an interval indicator 526 is placed on the filter 514. A cumulative indicator 522 is built onto one of the loops 518 at a position that will sit behind the wearer's ear. The cumulative indicator 522 includes a panel 523 that is translucent or transparent and a conductive strip 524 in thermal communication with a temperature measuring element such as a thermistor. The cumulative indicator 522 further includes a line of lighting elements, such as LED's, situated behind the panel 523. The lighting elements are controlled to illuminate as a function of the temperature measured through the conductive strip 524. As the measured temperature rises, and starting from either end of the panel 523, the panel 523 is illuminated at or to a point of increasing distance along the panel 523. For example, the lighting elements may be controlled to illuminate only a lower end of the panel 523 at a lower threshold temperature, and more or different lighting elements may be illuminated further up the panel 523 with increasing temperature measured through the strip 524. The panel 523 may have a color gradient from cooler to warmer colors, specifically from blue to red, from its lower end to its upper end, so that an observer may intuit the meaning of the progressive illumination of the panel 523. In alternative arrangements, the panel 523 may illuminate progressively from its upper end to its lower end, and has a corresponding color gradient from cooler to warmer colors from its upper end to its lower end. In yet further alternative arrangements, a cumulative indicator 522 as described in this paragraph can be located on other portions of the mask 510, such as sewn into a pocket on the filter 514.

The mask 510 is illustrated in FIG. 6A with a matte exterior of the filter 514. Thus, the filter 514 as illustrated in FIG. 6A is constructed either with an outer layer 70, or without and outer layer 70 but with the antiviral layer 66 being sprayed or printed only on the inward facing side with antiviral material. By contrast, the mask 510 as illustrated in FIG. 6B has no outer layer 70, and the antiviral layer 66 is printed or sprayed on the outward facing side, or dip coated entirely, with copper or another metallic antiviral substance.

Such construction provides the filter 514 as illustrated in FIG. 6B with a metallic sheen, and inhibits the accumulation of active viruses on the exterior of the filter 514.

In any instance in the foregoing description where an antiviral substance, material, coating, or property is discussed, alternative arrangements may substitute an antibacterial, antifungal, or generally antimicrobial substance, material, or property. The term "antimicrobial" is used to refer to any substance that has any one of or any combination of antiviral, antibacterial, and antifungal properties. Moreover, such substances, materials, and coatings may be applied to other articles. Personal apparel, including any clothing, or personal protective equipment such as gloves and shoes may be treated with any of the above described coatings. Hats, bags, and coats may be treated with the above described coatings as well. The coatings may also be applied to non-worn articles such as sheets, bedding, and air filters.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An article comprising:
 a fabric coated with a composition, the composition including:
  a thermoplastic resin comprising a thermoplastic hot melt adhesive comprising one or more of a copolyester or a copolyamid;
  oil having antiviral properties;
  a resinous binder comprising acrylic, wherein the resinous binder is an uncrosslinked polymer in a solid, cured state;
  an emulsifier; and
  metal or metal oxide particles having antiviral properties,
 wherein the fabric is folded and adhered to itself by the hot melt adhesive.

2. The article of claim 1, wherein the oil comprises cinnamon oil, tea tree oil, eucalyptus oil, thyme oil, and/or clove oil.

3. The article of claim 1, wherein the fabric is a nonwoven fabric.

4. The article of claim 3, wherein the composition includes more oil than metal by weight.

5. The article of claim 1, wherein the emulsifier is 0.1% to 2% of the composition by weight.

6. The article of claim 1, wherein the oil comprises an essential oil from which an aromatic fraction has been removed.

7. The article of claim 5, wherein the oil is present in an amount from 12% to 24% of the composition by weight.

8. The article of claim 1, wherein the article comprises a face mask and the fabric comprises a portion of an air-permeable filter of the face mask, the air-permeable filter of the face mask having a wearer-facing side that is free of the coating.

9. A face mask comprising:
 an air-permeable fabric configured to be placed on a user's face,
 a composition arranged on the fabric, the composition including a thermoplastic resin comprising a thermoplastic hot melt adhesive comprising one or more of a copolyester or a copolyamid, metal or metal oxide particles having antiviral properties dispersed within the resin, an emulsifier dispersed within the resin, oil having antiviral properties dispersed within the resin, and an acrylic resinous binder dispersed within the resin, wherein the resinous binder is an uncrosslinked polymer in a solid, cured state,
 wherein the fabric is folded and adhered to itself by the hot melt adhesive.

10. The face mask of claim 9, wherein the metal comprises copper.

11. The face mask of claim 9, wherein the metal oxide comprises copper oxide.

12. The face mask of claim 11, further comprising a temperature indicator.

13. The face mask of claim 12, wherein the temperature indicator comprises thermochromic ink or an electronic lighting element.

14. The face mask of claim 13, wherein the temperature indicator comprises a thermistor.

15. The face mask of claim 9, wherein the composition has a surface and the oil is unstable within the composition such that the oil gradually migrates to the surface.

16. The face mask of claim 9, wherein the composition comprises a total weight of 2 to 3 grams.

17. The face mask of claim 9, wherein the fabric has an inner side free of the composition and configured to be placed adjacent a user's face and an outer side, the composition being arranged on the outer side of the fabric.

18. The face mask of claim 17, wherein the fabric has upper and lower edges and includes coating-free regions at the upper and lower edges.

19. The article of claim 1, wherein the article comprises a face mask, wherein the fabric has upper and lower edges and includes coating-free regions at the upper and lower edges.

* * * * *